(12) United States Patent
Ruane et al.

(10) Patent No.: US 12,397,141 B2
(45) Date of Patent: Aug. 26, 2025

(54) THERMALLY REGULATED TRANSDERMAL DRUG DELIVERY SYSTEM

(71) Applicant: MORNINGSIDE VENTURE INVESTMENTS LIMITED, Newton Centre, MA (US)

(72) Inventors: Patrick H. Ruane, Dublin, CA (US); Jackie Joe Hancock, Berkeley, CA (US); Anubhav Arora, Hayward, CA (US)

(73) Assignee: Morningside Venture Investments Limited, Monaco (MC)

( * ) Notice: Subject to any disclaimer, the term of this patent is extended or adjusted under 35 U.S.C. 154(b) by 668 days.

(21) Appl. No.: 17/293,570

(22) PCT Filed: Nov. 15, 2019

(86) PCT No.: PCT/US2019/061761
§ 371 (c)(1),
(2) Date: May 13, 2021

(87) PCT Pub. No.: WO2020/102695
PCT Pub. Date: May 22, 2020

(65) Prior Publication Data
US 2022/0001158 A1 Jan. 6, 2022

Related U.S. Application Data

(60) Provisional application No. 62/768,768, filed on Nov. 16, 2018.

(51) Int. Cl.
*A61M 37/00* (2006.01)
*A61K 31/465* (2006.01)

(52) U.S. Cl.
CPC .......... *A61M 37/00* (2013.01); *A61K 31/465* (2013.01); *A61M 2037/0007* (2013.01);
(Continued)

(58) Field of Classification Search
CPC .......... A61M 37/00; A61M 2037/0007; A61M 2205/055; A61M 2205/3606;
(Continued)

(56) References Cited

U.S. PATENT DOCUMENTS 2,183,482 A 12/1939 Kurkjian
3,279,653 A 10/1966 Pfleger
(Continued)

FOREIGN PATENT DOCUMENTS

AU 662877 B3 9/1995
BE 899037 A 6/1984
(Continued)

OTHER PUBLICATIONS

Abood et al.; Structure-activity studies of carbamate and other esters: agonists and antagonists to nicotine; Pharmacology Biochemistry and Behavior; 30(2); pp. 403-408; Jun. 1988.
(Continued)

*Primary Examiner* — Susan S Su
*Assistant Examiner* — Erin A Kim
(74) *Attorney, Agent, or Firm* — Shay Glenn LLP

(57) ABSTRACT

Described herein are drug and other active agent transdermal delivery systems and devices to deliver active agents to skin or mucosa of a subject, and methods of delivering such active agents. In particular, systems, methods, and devices are described that control the concentration and timing of active agent delivery. Such systems or devices may include a transdermal membrane and a temperature control element for heating and/or cooling a portion of the transdermal delivery system to provide pulsatile active agent delivery through the transdermal membrane.

32 Claims, 4 Drawing Sheets

(52) U.S. Cl.
CPC .............. *A61M 2205/055* (2013.01); *A61M 2205/3606* (2013.01); *A61M 2205/368* (2013.01); *A61M 2205/8206* (2013.01)

(58) Field of Classification Search
CPC .... A61M 2205/368; A61M 2205/8206; A61K 31/465; A61K 9/0009; A61K 9/0014; A61K 9/0097; A61K 9/7038; A61F 13/00063
See application file for complete search history.

(56) References Cited

U.S. PATENT DOCUMENTS

| | | |
|---|---|---|
| 3,845,217 A | 10/1974 | Ferno et al. |
| 4,313,439 A | 2/1982 | Babb et al. |
| 4,321,387 A | 3/1982 | Chavdarian et al. |
| 4,327,725 A | 5/1982 | Cortese et al. |
| 4,332,945 A | 6/1982 | Edwards |
| 4,379,454 A | 4/1983 | Campbell et al. |
| 4,545,990 A | 10/1985 | Le Foyer de Costil et al. |
| 4,579,858 A | 4/1986 | Ferno et al. |
| 4,590,278 A | 5/1986 | Edwards |
| 4,597,961 A | 7/1986 | Etscorn |
| 4,708,716 A | 11/1987 | Sibalis |
| 4,772,263 A | 9/1988 | Dorman et al. |
| 4,806,356 A | 2/1989 | Shaw |
| 4,853,854 A | 8/1989 | Behar et al. |
| 4,885,154 A | 12/1989 | Cormier et al. |
| 4,908,213 A | 3/1990 | Govil et al. |
| 4,917,676 A | 4/1990 | Heiber et al. |
| 4,917,895 A | 4/1990 | Lee et al. |
| 4,920,989 A | 5/1990 | Rose et al. |
| 4,952,928 A | 8/1990 | Carroll et al. |
| 4,953,572 A | 9/1990 | Rose et al. |
| 4,992,445 A | 2/1991 | Lawter et al. |
| 4,994,278 A * | 2/1991 | Sablotsky ............ A61K 9/7038 424/447 |
| 5,000,956 A | 3/1991 | Amkraut et al. |
| 5,001,139 A | 3/1991 | Lawter et al. |
| 5,013,293 A | 5/1991 | Sibalis |
| 5,023,252 A | 6/1991 | Hseih |
| 5,049,387 A | 9/1991 | Amkraut |
| 5,069,904 A | 12/1991 | Masterson |
| 5,073,380 A | 12/1991 | Babu et al. |
| 5,097,834 A | 3/1992 | Skrabal |
| 5,120,545 A | 6/1992 | Ledger et al. |
| 5,130,139 A | 7/1992 | Cormier et al. |
| 5,149,538 A | 9/1992 | Granger et al. |
| 5,149,719 A | 9/1992 | Ferber et al. |
| 5,212,188 A | 5/1993 | Caldwell et al. |
| 5,221,254 A | 6/1993 | Phipps |
| 5,227,391 A | 7/1993 | Caldwell et al. |
| 5,232,704 A | 8/1993 | Franz et al. |
| 5,232,933 A | 8/1993 | Lippiello et al. |
| 5,236,714 A | 8/1993 | Lee et al. |
| 5,242,934 A | 9/1993 | Lippiello et al. |
| 5,242,935 A | 9/1993 | Lippiello et al. |
| 5,242,941 A | 9/1993 | Lewy et al. |
| 5,248,690 A | 9/1993 | Caldwel et al. |
| 5,252,604 A | 10/1993 | Nagy et al. |
| 5,262,165 A | 11/1993 | Govil et al. |
| 5,273,755 A | 12/1993 | Venkatraman et al. |
| 5,273,756 A | 12/1993 | Fallon et al. |
| 5,304,739 A | 4/1994 | Klug et al. |
| 5,310,404 A | 5/1994 | Gyory et al. |
| 5,352,456 A | 10/1994 | Fallon et al. |
| 5,364,630 A | 11/1994 | Osborne et al. |
| 5,370,635 A | 12/1994 | Strausak et al. |
| 5,388,571 A | 2/1995 | Roberts et al. |
| 5,389,679 A | 2/1995 | Alliger |
| 5,393,526 A | 2/1995 | Castro |
| 5,405,614 A | 4/1995 | D'Angelo et al. |
| 5,415,629 A | 5/1995 | Henley |
| 5,445,609 A | 8/1995 | Lattin et al. |
| 5,451,407 A | 9/1995 | Cormier et al. |
| 5,464,387 A | 11/1995 | Haak et al. |
| 5,472,946 A | 12/1995 | Peck et al. |
| 5,501,697 A | 3/1996 | Fisher |
| 5,505,958 A | 4/1996 | Bello et al. |
| 5,512,306 A | 4/1996 | Carlsson et al. |
| 5,516,793 A | 5/1996 | Duffy |
| 5,525,351 A | 6/1996 | Dam |
| 5,545,407 A | 8/1996 | Hall et al. |
| 5,562,607 A | 10/1996 | Gyory |
| 5,596,994 A | 1/1997 | Bro |
| 5,601,839 A | 2/1997 | Quan et al. |
| 5,616,332 A | 4/1997 | Herstein |
| 5,618,557 A | 4/1997 | Wille et al. |
| 5,653,682 A | 8/1997 | Sibalis |
| 5,656,255 A | 8/1997 | Jones |
| 5,662,920 A | 9/1997 | Santus |
| 5,686,100 A | 11/1997 | Wille et al. |
| 5,688,232 A | 11/1997 | Flower |
| 5,697,896 A | 12/1997 | McNichols et al. |
| 5,716,987 A | 2/1998 | Wille |
| 5,722,418 A | 3/1998 | Bro |
| 5,733,259 A | 3/1998 | Valcke et al. |
| 5,785,688 A | 7/1998 | Joshi et al. |
| 5,797,867 A | 8/1998 | Guerrera et al. |
| 5,820,875 A | 10/1998 | Fallon et al. |
| 5,833,466 A | 11/1998 | Borg |
| 5,843,979 A | 12/1998 | Wille et al. |
| 5,846,559 A | 12/1998 | Hopp |
| 5,865,786 A | 2/1999 | Sibalis et al. |
| 5,876,368 A | 3/1999 | Flower |
| 5,879,292 A | 3/1999 | Sternberg et al. |
| 5,879,322 A | 3/1999 | Lattin et al. |
| 5,882,676 A | 3/1999 | Lee et al. |
| 5,908,301 A | 6/1999 | Lutz |
| 5,919,156 A | 7/1999 | Stropkay et al. |
| 5,932,240 A | 8/1999 | D'Angelo et al. |
| 5,945,123 A | 8/1999 | Hermelin |
| 5,967,789 A | 10/1999 | Segel et al. |
| 5,972,389 A | 10/1999 | Shell et al. |
| 5,993,435 A | 11/1999 | Haak et al. |
| 5,997,501 A | 12/1999 | Gross et al. |
| 6,018,679 A | 1/2000 | Dinh et al. |
| 6,019,997 A | 2/2000 | Scholz et al. |
| 6,024,981 A | 2/2000 | Khankari et al. |
| 6,034,079 A | 3/2000 | Sanberg et al. |
| 6,059,736 A | 5/2000 | Tapper |
| 6,059,753 A | 5/2000 | Faust et al. |
| 6,068,853 A | 5/2000 | Giannos et al. |
| 6,081,734 A | 6/2000 | Batz |
| 6,090,404 A | 7/2000 | Meconi et al. |
| 6,093,419 A | 7/2000 | Rolf |
| 6,120,803 A | 9/2000 | Wong et al. |
| 6,129,702 A | 10/2000 | Woias et al. |
| 6,162,214 A | 12/2000 | Mueller et al. |
| 6,165,155 A | 12/2000 | Jacobsen et al. |
| 6,211,194 B1 | 4/2001 | Westman et al. |
| 6,211,296 B1 | 4/2001 | Frate et al. |
| 6,221,394 B1 | 4/2001 | Gilbert et al. |
| 6,238,689 B1 | 5/2001 | Rhodes et al. |
| 6,274,606 B1 | 8/2001 | Caldwell et al. |
| 6,310,102 B1 | 10/2001 | Dull et al. |
| 6,365,182 B1 | 4/2002 | Khankari et al. |
| 6,368,625 B1 | 4/2002 | Siebert et al. |
| 6,374,136 B1 | 4/2002 | Murdock |
| 6,416,471 B1 | 7/2002 | Kumar et al. |
| 6,417,359 B1 | 7/2002 | Crooks et al. |
| 6,423,747 B1 | 7/2002 | Lanzendörfer et al. |
| 6,436,078 B1 | 8/2002 | Svedman |
| 6,437,004 B1 | 8/2002 | Perricone |
| 6,454,708 B1 | 9/2002 | Ferguson et al. |
| 6,488,959 B2 | 12/2002 | Stanley et al. |
| 6,492,399 B1 | 12/2002 | Dull et al. |
| 6,539,250 B1 | 3/2003 | Bettinger |
| 6,546,281 B1 | 4/2003 | Zhang et al. |
| 6,567,785 B2 | 5/2003 | Clendenon |
| 6,569,449 B1 | 5/2003 | Stinchcomb et al. |
| 6,569,866 B2 | 5/2003 | Simon |
| 6,576,269 B1 | 6/2003 | Korneyev |
| 6,579,865 B2 | 6/2003 | Mak et al. |

(56) References Cited

U.S. PATENT DOCUMENTS

| | | |
|---|---|---|
| 6,589,229 B1 | 7/2003 | Connelly et al. |
| 6,595,956 B1 | 7/2003 | Gross et al. |
| 6,638,528 B1 | 10/2003 | Kanios |
| 6,638,543 B2 | 10/2003 | Kang et al. |
| 6,660,295 B2 | 12/2003 | Watanabe et al. |
| 6,689,380 B1 | 2/2004 | Marchitto et al. |
| 6,723,086 B2 | 4/2004 | Bassuk et al. |
| 6,723,340 B2 | 4/2004 | Gusler et al. |
| 6,746,688 B1 | 6/2004 | Kushnir et al. |
| 6,791,003 B1 | 9/2004 | Choi et al. |
| 6,799,576 B2 | 10/2004 | Farr |
| 6,849,645 B2 | 2/2005 | Majeed et al. |
| 6,861,066 B2 | 3/2005 | Van de Casteele |
| 6,867,342 B2 | 3/2005 | Johnston et al. |
| 6,887,202 B2 | 5/2005 | Currie et al. |
| 6,893,655 B2 | 5/2005 | Flanigan et al. |
| 6,900,202 B2 | 5/2005 | Imoto et al. |
| 6,911,475 B1 | 6/2005 | Villafane et al. |
| 6,998,176 B2 | 2/2006 | Morita et al. |
| 7,011,843 B2 | 3/2006 | Becher et al. |
| 7,011,849 B2 | 3/2006 | Storm et al. |
| 7,019,622 B2 | 3/2006 | Orr et al. |
| 7,064,143 B1 | 6/2006 | Gurley et al. |
| 7,182,955 B2 | 2/2007 | Hart et al. |
| 7,196,619 B2 | 3/2007 | Perlman et al. |
| 7,229,641 B2 | 6/2007 | Cherukuri |
| 7,282,217 B1 | 10/2007 | Grimshaw et al. |
| 7,332,182 B2 | 2/2008 | Sackler |
| 7,376,700 B1 | 5/2008 | Clark et al. |
| 7,384,651 B2 | 6/2008 | Hille et al. |
| 7,384,653 B2 | 6/2008 | Wright et al. |
| 7,579,019 B2 | 8/2009 | Tapolsky et al. |
| 7,598,275 B2 | 10/2009 | Cooke et al. |
| 7,718,677 B2 | 5/2010 | Quik et al. |
| 7,780,981 B2 | 8/2010 | DiPierro et al. |
| 7,931,563 B2 | 4/2011 | Shaw et al. |
| 7,988,660 B2 | 8/2011 | Byland et al. |
| 8,003,080 B2 | 8/2011 | Rabinowitz et al. |
| 8,021,334 B2 | 9/2011 | Shekalim |
| 8,137,314 B2 | 3/2012 | Mounce et al. |
| 8,140,143 B2 | 3/2012 | Picard et al. |
| 8,192,756 B2 | 6/2012 | Berner et al. |
| 8,246,581 B2 | 8/2012 | Adams et al. |
| 8,252,321 B2 | 8/2012 | DiPierro et al. |
| 8,262,394 B2 | 9/2012 | Walker et al. |
| 8,268,475 B2 | 9/2012 | Tucholski |
| 8,285,328 B2 | 10/2012 | Caffey et al. |
| 8,303,500 B2 | 11/2012 | Raheman |
| 8,309,568 B2 | 11/2012 | Stinchcomb et al. |
| 8,372,040 B2 | 2/2013 | Huang et al. |
| 8,414,532 B2 | 4/2013 | Brandt et al. |
| 8,440,220 B2 | 5/2013 | Gale et al. |
| 8,440,221 B2 | 5/2013 | Zumbrunn et al. |
| 8,441,411 B2 | 5/2013 | Tucholski et al. |
| 8,445,010 B2 | 5/2013 | Anderson et al. |
| 8,449,471 B2 | 5/2013 | Tran |
| 8,517,988 B2 | 8/2013 | Smith |
| 8,545,445 B2 | 10/2013 | Kamen et al. |
| 8,574,188 B2 | 11/2013 | Potter et al. |
| 8,586,079 B2 | 11/2013 | Hansted et al. |
| 8,589,174 B2 | 11/2013 | Nelson et al. |
| 8,614,278 B2 | 12/2013 | Loubert et al. |
| 8,632,497 B2 | 1/2014 | Yodfat et al. |
| 8,666,781 B2 | 3/2014 | Hanina et al. |
| 8,673,346 B2 | 3/2014 | Zumbrunn et al. |
| 8,684,922 B2 | 4/2014 | Tran |
| 8,688,189 B2 | 4/2014 | Shennib |
| 8,690,827 B2 | 4/2014 | Edwards et al. |
| 8,690,865 B2 | 4/2014 | Prausnitz et al. |
| 8,696,637 B2 | 4/2014 | Ross |
| 8,703,175 B2 | 4/2014 | Kanios et al. |
| 8,703,177 B2 | 4/2014 | Finn et al. |
| 8,722,233 B2 | 5/2014 | Tucholski |
| 8,727,745 B2 | 5/2014 | Rush et al. |
| 8,741,336 B2 | 6/2014 | DiPierro et al. |
| 8,747,348 B2 | 6/2014 | Yodfat et al. |
| 8,753,315 B2 | 6/2014 | Alferness et al. |
| 8,773,257 B2 | 7/2014 | Yodfat et al. |
| 8,814,822 B2 | 8/2014 | Yodfat et al. |
| 8,862,223 B2 | 10/2014 | Yanaki |
| 8,864,727 B2 | 10/2014 | Lee |
| 8,865,207 B2 | 10/2014 | Kanios et al. |
| 8,872,663 B2 | 10/2014 | Forster |
| 8,876,802 B2 | 11/2014 | Grigorov |
| 8,956,644 B2 | 2/2015 | Yum et al. |
| 8,962,014 B2 | 2/2015 | Prinz et al. |
| 8,986,253 B2 | 3/2015 | DiPerna |
| 8,999,356 B1 | 4/2015 | Ramirez et al. |
| 8,999,372 B2 | 4/2015 | Davidson et al. |
| 9,023,392 B2 | 5/2015 | Koo et al. |
| 9,044,582 B2 | 6/2015 | Chang et al. |
| 9,050,348 B2 | 6/2015 | Kydonieus et al. |
| 9,078,833 B2 | 7/2015 | Audett |
| 9,111,085 B1 | 8/2015 | Darmour et al. |
| 9,114,240 B2 | 8/2015 | Horstmann et al. |
| 9,155,712 B2 | 10/2015 | Kanios et al. |
| 9,233,203 B2 | 1/2016 | Moberg et al. |
| 9,238,001 B2 | 1/2016 | Weyer et al. |
| 9,238,108 B2 | 1/2016 | Edwards et al. |
| 9,248,104 B2 | 2/2016 | Valia et al. |
| 9,289,397 B2 | 3/2016 | Wright |
| 9,308,202 B2 | 4/2016 | Hille et al. |
| 9,314,527 B2 | 4/2016 | Cottrell et al. |
| 9,373,269 B2 | 6/2016 | Bergman et al. |
| 9,380,698 B1 | 6/2016 | Li et al. |
| RE46,217 E | 11/2016 | Huang et al. |
| 9,513,666 B2 | 12/2016 | Li et al. |
| 9,549,903 B2 | 1/2017 | Hille et al. |
| 9,555,226 B2 | 1/2017 | Zumbrunn et al. |
| 9,555,227 B2 | 1/2017 | Dipierro |
| 9,555,277 B2 | 1/2017 | Yeh |
| 9,623,017 B2 | 4/2017 | Barbier et al. |
| 9,636,457 B2 | 5/2017 | Newberry et al. |
| 9,655,843 B2 | 5/2017 | Finn et al. |
| 9,656,441 B2 | 5/2017 | LeDonne et al. |
| 9,669,199 B2 | 6/2017 | DiPierro et al. |
| 9,687,186 B2 | 6/2017 | Goldstein et al. |
| 9,693,689 B2 | 7/2017 | Gannon et al. |
| 9,700,552 B2 | 7/2017 | Weimann |
| 9,717,698 B2 | 8/2017 | Horstmann et al. |
| 9,735,893 B1 | 8/2017 | Aleksov et al. |
| 9,782,082 B2 | 10/2017 | Gannon et al. |
| 9,795,681 B2 | 10/2017 | Abreu |
| 9,867,539 B2 | 1/2018 | Heikenfeld et al. |
| 9,895,320 B2 | 2/2018 | Ogino et al. |
| 9,949,935 B2 | 4/2018 | Murata |
| 9,974,492 B1 | 5/2018 | Dicks et al. |
| 9,993,203 B2 | 6/2018 | Mei et al. |
| 10,004,447 B2 | 6/2018 | Shen et al. |
| 10,034,841 B2 | 7/2018 | Müller et al. |
| 10,105,487 B2 | 10/2018 | DiPierro et al. |
| 10,143,687 B2 | 12/2018 | Azhir |
| 10,213,586 B2 | 2/2019 | Netzel et al. |
| 10,232,156 B2 | 3/2019 | Netzel et al. |
| 10,258,738 B2 | 4/2019 | Dipierro et al. |
| 10,258,778 B2 | 4/2019 | DiPierro et al. |
| 10,679,516 B2 | 6/2020 | Darmour et al. |
| 10,716,764 B2 | 7/2020 | Zumbrunn et al. |
| 2001/0022978 A1 | 9/2001 | Lacharriere et al. |
| 2001/0026788 A1 | 10/2001 | Piskorz |
| 2002/0002189 A1 | 1/2002 | Smith et al. |
| 2002/0034535 A1 | 3/2002 | Kleiner et al. |
| 2002/0106329 A1 | 8/2002 | Leslie |
| 2002/0127256 A1 | 9/2002 | Murad |
| 2002/0165170 A1 | 11/2002 | Wilson et al. |
| 2002/0169439 A1 | 11/2002 | Flaherty |
| 2002/0182238 A1 | 12/2002 | Creton |
| 2003/0004187 A1 | 1/2003 | Bedard et al. |
| 2003/0065294 A1 | 4/2003 | Pickup et al. |
| 2003/0065924 A1 | 4/2003 | Wuidart et al. |
| 2003/0083645 A1 | 5/2003 | Angel et al. |
| 2003/0087937 A1 | 5/2003 | Lindberg |
| 2003/0119879 A1 | 6/2003 | Landh et al. |

(56) References Cited

U.S. PATENT DOCUMENTS

| | | |
|---|---|---|
| 2003/0138464 A1* | 7/2003 | Zhang .................. A61K 9/0024 604/20 |
| 2003/0159702 A1 | 8/2003 | Lindell et al. |
| 2004/0019321 A1 | 1/2004 | Sage et al. |
| 2004/0034068 A1 | 2/2004 | Warchol et al. |
| 2004/0037879 A1 | 2/2004 | Adusumilli et al. |
| 2004/0052843 A1 | 3/2004 | Lerner et al. |
| 2004/0062802 A1 | 4/2004 | Hermelin |
| 2004/0138074 A1 | 7/2004 | Ahmad et al. |
| 2004/0166159 A1 | 8/2004 | Han et al. |
| 2004/0191322 A1 | 9/2004 | Hansson |
| 2004/0194793 A1 | 10/2004 | Lindell et al. |
| 2004/0219192 A1 | 11/2004 | Horstmann et al. |
| 2004/0229908 A1 | 11/2004 | Nelson |
| 2004/0241218 A1 | 12/2004 | Tavares et al. |
| 2004/0253249 A1 | 12/2004 | Rudnic et al. |
| 2004/0259816 A1 | 12/2004 | Pandol et al. |
| 2005/0002806 A1 | 1/2005 | Fuechslin et al. |
| 2005/0014779 A1 | 1/2005 | Papke |
| 2005/0021092 A1 | 1/2005 | Yun et al. |
| 2005/0034842 A1 | 2/2005 | Huber et al. |
| 2005/0048020 A1 | 3/2005 | Wille |
| 2005/0053665 A1 | 3/2005 | Ek et al. |
| 2005/0113452 A1 | 5/2005 | Flashner Barak et al. |
| 2005/0141346 A1 | 6/2005 | Rawls et al. |
| 2005/0151110 A1 | 7/2005 | Minor et al. |
| 2005/0159419 A1 | 7/2005 | Stephenson et al. |
| 2005/0197625 A1 | 9/2005 | Haueter et al. |
| 2005/0266032 A1 | 12/2005 | Srinivasan et al. |
| 2005/0276852 A1 | 12/2005 | Davis et al. |
| 2006/0024358 A1 | 2/2006 | Santini et al. |
| 2006/0036209 A1 | 2/2006 | Subramony et al. |
| 2006/0057202 A1 | 3/2006 | Antarkar et al. |
| 2006/0122577 A1 | 6/2006 | Poulsen et al. |
| 2006/0135911 A1* | 6/2006 | Mittur .................. A61F 7/007 604/113 |
| 2006/0167039 A1 | 7/2006 | Nguyen et al. |
| 2006/0173439 A1 | 8/2006 | Thorne et al. |
| 2006/0184093 A1 | 8/2006 | Phipps et al. |
| 2006/0188859 A1 | 8/2006 | Yakobi |
| 2006/0204578 A1 | 9/2006 | Vergez et al. |
| 2006/0206054 A1 | 9/2006 | Shekalim |
| 2007/0026054 A1 | 2/2007 | Theobald et al. |
| 2007/0042026 A1 | 2/2007 | Wille |
| 2007/0065365 A1 | 3/2007 | Kugelmann et al. |
| 2007/0086275 A1 | 4/2007 | Robinson et al. |
| 2007/0088338 A1 | 4/2007 | Ehwald et al. |
| 2007/0104787 A1 | 5/2007 | Posey Dowty et al. |
| 2007/0149952 A1 | 6/2007 | Bland et al. |
| 2007/0154336 A1 | 7/2007 | Miyazaki et al. |
| 2007/0168501 A1 | 7/2007 | Cobb et al. |
| 2007/0179172 A1 | 8/2007 | Becker et al. |
| 2007/0191815 A1 | 8/2007 | DiPierro |
| 2007/0250018 A1 | 10/2007 | Adachi et al. |
| 2007/0255195 A1 | 11/2007 | Adachi |
| 2007/0256684 A1 | 11/2007 | Kelliher et al. |
| 2007/0260491 A1 | 11/2007 | Palmer et al. |
| 2007/0279217 A1 | 12/2007 | Venkatraman et al. |
| 2007/0299401 A1 | 12/2007 | Alferness et al. |
| 2008/0008747 A1 | 1/2008 | Royds |
| 2008/0015494 A1 | 1/2008 | Santini et al. |
| 2008/0045879 A1* | 2/2008 | Prausnitz ............. A61B 18/082 606/41 |
| 2008/0131494 A1 | 6/2008 | Reed et al. |
| 2008/0138294 A1 | 6/2008 | Gonda |
| 2008/0138398 A1 | 6/2008 | Gonda |
| 2008/0138399 A1 | 6/2008 | Gonda |
| 2008/0138423 A1 | 6/2008 | Gonda |
| 2008/0139907 A1 | 6/2008 | Rao et al. |
| 2008/0152592 A1 | 6/2008 | Rebec |
| 2008/0195946 A1 | 8/2008 | Peri-Glass |
| 2008/0201174 A1 | 8/2008 | Ramasubramanian et al. |
| 2008/0233178 A1 | 9/2008 | Reidenberg et al. |
| 2008/0274168 A1 | 11/2008 | Baker et al. |
| 2008/0319272 A1 | 12/2008 | Patangay et al. |
| 2009/0005009 A1 | 1/2009 | Marsili |
| 2009/0010998 A1 | 1/2009 | Marchitto et al. |
| 2009/0024004 A1 | 1/2009 | Yang |
| 2009/0028824 A1 | 1/2009 | Chiang et al. |
| 2009/0062754 A1 | 3/2009 | Tang |
| 2009/0118710 A1 | 5/2009 | Kortzeborn |
| 2009/0169631 A1 | 7/2009 | Zamloot et al. |
| 2009/0246265 A1 | 10/2009 | Stinchcomb et al. |
| 2009/0247985 A1 | 10/2009 | Melsheimer et al. |
| 2009/0259176 A1 | 10/2009 | Yairi |
| 2009/0299156 A1 | 12/2009 | Simpson et al. |
| 2010/0003653 A1 | 1/2010 | Brown |
| 2010/0010443 A1 | 1/2010 | Morgan et al. |
| 2010/0068250 A1 | 3/2010 | Anderson et al. |
| 2010/0114008 A1 | 5/2010 | Marchitto et al. |
| 2010/0130932 A1 | 5/2010 | Yodfat et al. |
| 2010/0145303 A1 | 6/2010 | Yodfat et al. |
| 2010/0179473 A1 | 7/2010 | Genosar |
| 2010/0196463 A1 | 8/2010 | Quik et al. |
| 2010/0198187 A1 | 8/2010 | Yodfat et al. |
| 2010/0211005 A1 | 8/2010 | Edwards et al. |
| 2010/0248198 A1 | 9/2010 | Seidman et al. |
| 2010/0273738 A1 | 10/2010 | Valcke et al. |
| 2010/0280432 A1 | 11/2010 | DiPierro et al. |
| 2011/0004072 A1 | 1/2011 | Fletcher et al. |
| 2011/0053129 A1 | 3/2011 | Basson et al. |
| 2011/0054285 A1 | 3/2011 | Searle et al. |
| 2011/0109439 A1 | 5/2011 | Borlenghi |
| 2011/0137255 A1 | 6/2011 | Nielsen et al. |
| 2011/0152635 A1 | 6/2011 | Morris et al. |
| 2011/0153360 A1 | 6/2011 | Hanina et al. |
| 2011/0160640 A1 | 6/2011 | Yanaki |
| 2011/0160655 A1 | 6/2011 | Hanson et al. |
| 2011/0212027 A1* | 9/2011 | Hoare .................. A61K 9/0024 424/9.1 |
| 2011/0241446 A1 | 10/2011 | Tucholski |
| 2011/0245633 A1 | 10/2011 | Goldberg et al. |
| 2011/0245783 A1 | 10/2011 | Stinchcomb et al. |
| 2011/0250576 A1 | 10/2011 | Hester |
| 2011/0256517 A1 | 10/2011 | Swanson |
| 2011/0264028 A1 | 10/2011 | Ramdas et al. |
| 2011/0268809 A1 | 11/2011 | Brinkley et al. |
| 2011/0275987 A1 | 11/2011 | Caffey et al. |
| 2012/0046644 A1 | 2/2012 | Ziaie et al. |
| 2012/0078216 A1 | 3/2012 | Smith et al. |
| 2012/0123387 A1 | 5/2012 | Gonzalez et al. |
| 2012/0156138 A1 | 6/2012 | Smith |
| 2012/0171277 A1 | 7/2012 | Royds |
| 2012/0178065 A1 | 7/2012 | Naghavi et al. |
| 2012/0191043 A1 | 7/2012 | Yodfat et al. |
| 2012/0203573 A1 | 8/2012 | Mayer et al. |
| 2012/0209223 A1 | 8/2012 | Salman et al. |
| 2012/0221251 A1 | 8/2012 | Rosenberg et al. |
| 2012/0244503 A1 | 9/2012 | Neveldine |
| 2012/0302844 A1 | 11/2012 | Schnidrig et al. |
| 2012/0316896 A1 | 12/2012 | Rahman et al. |
| 2012/0329017 A1 | 12/2012 | Pham |
| 2013/0017259 A1 | 1/2013 | Azhir |
| 2013/0041258 A1 | 2/2013 | Patrick et al. |
| 2013/0096495 A1 | 4/2013 | Holmqvist et al. |
| 2013/0123719 A1 | 5/2013 | Mao et al. |
| 2013/0158430 A1 | 6/2013 | Aceti et al. |
| 2013/0178826 A1 | 7/2013 | Li |
| 2013/0190683 A1 | 7/2013 | Hanson et al. |
| 2013/0216989 A1 | 8/2013 | Cuthbert |
| 2013/0253430 A1 | 9/2013 | Kouyoumjian et al. |
| 2013/0302398 A1 | 11/2013 | Ambati et al. |
| 2013/0311917 A1 | 11/2013 | Bar-or et al. |
| 2013/0317384 A1 | 11/2013 | Le |
| 2013/0328572 A1 | 12/2013 | Wang et al. |
| 2013/0345633 A1 | 12/2013 | Chong |
| 2014/0039396 A1 | 2/2014 | Geipel et al. |
| 2014/0046288 A1 | 2/2014 | Geipel et al. |
| 2014/0073883 A1 | 3/2014 | Rao et al. |
| 2014/0088554 A1 | 3/2014 | Li et al. |
| 2014/0099614 A1 | 4/2014 | Hu et al. |
| 2014/0100241 A1 | 4/2014 | Slater et al. |
| 2014/0163521 A1 | 6/2014 | O'Conner |
| 2014/0200525 A1 | 7/2014 | DiPierro |

(56) References Cited

U.S. PATENT DOCUMENTS

| | | |
|---|---|---|
| 2014/0206327 A1 | 7/2014 | Ziemianska et al. |
| 2014/0207047 A1 | 7/2014 | DiPierro et al. |
| 2014/0228736 A1 | 8/2014 | Eppstein et al. |
| 2014/0237028 A1 | 8/2014 | Messenger et al. |
| 2014/0240124 A1 | 8/2014 | Bychkov |
| 2014/0266584 A1 | 9/2014 | Ingle et al. |
| 2014/0272844 A1 | 9/2014 | Hendriks et al. |
| 2014/0272845 A1 | 9/2014 | Hendriks et al. |
| 2014/0272846 A1 | 9/2014 | Richling |
| 2014/0275135 A1 | 9/2014 | Genov et al. |
| 2014/0275932 A1 | 9/2014 | Zadig |
| 2014/0276127 A1 | 9/2014 | Ferdosi et al. |
| 2014/0279740 A1 | 9/2014 | Wernevi et al. |
| 2014/0302121 A1 | 10/2014 | Bevier |
| 2014/0303574 A1 | 10/2014 | Knutson |
| 2014/0365408 A1 | 12/2014 | Snyder et al. |
| 2014/0378943 A1 | 12/2014 | Geipel |
| 2015/0057616 A1 | 2/2015 | Shergold et al. |
| 2015/0209783 A1 | 7/2015 | Ingber et al. |
| 2015/0273148 A1 | 10/2015 | Sexton et al. |
| 2015/0310760 A1 | 10/2015 | Knotts et al. |
| 2015/0322939 A1 | 11/2015 | Katase |
| 2015/0342900 A1 | 12/2015 | Putnins |
| 2016/0030412 A1 | 2/2016 | Azhir |
| 2016/0058939 A1 | 3/2016 | Brewer et al. |
| 2016/0220553 A1 | 8/2016 | Azhir |
| 2016/0227361 A1 | 8/2016 | Booth et al. |
| 2016/0228383 A1 | 8/2016 | Zhang et al. |
| 2016/0235732 A1 | 8/2016 | Quik et al. |
| 2016/0235916 A1 | 8/2016 | Edwards et al. |
| 2016/0263312 A1 | 9/2016 | Junod et al. |
| 2016/0310664 A1 | 10/2016 | McKenzie et al. |
| 2016/0317057 A1 | 11/2016 | Li et al. |
| 2016/0317738 A1 | 11/2016 | Cross et al. |
| 2016/0339174 A1 | 11/2016 | Shapley et al. |
| 2016/0346456 A1 | 12/2016 | Cefai et al. |
| 2016/0346462 A1 | 12/2016 | Adams et al. |
| 2017/0007550 A1 | 1/2017 | Enscore et al. |
| 2017/0079932 A1 | 3/2017 | Emgenbroich et al. |
| 2017/0100573 A1 | 4/2017 | DiPierro |
| 2017/0189348 A1 | 7/2017 | Lee et al. |
| 2017/0189534 A1 | 7/2017 | Lee et al. |
| 2017/0207825 A1 | 7/2017 | Belogolovy |
| 2017/0209429 A1 | 7/2017 | Stinchcomb et al. |
| 2017/0232192 A1 | 8/2017 | Sasaki |
| 2017/0249433 A1 | 8/2017 | Hagen et al. |
| 2017/0296107 A1 | 10/2017 | Reid et al. |
| 2017/0296317 A1 | 10/2017 | Gordon |
| 2017/0351840 A1 | 12/2017 | Goguen |
| 2018/0014783 A1 | 1/2018 | Shi et al. |
| 2018/0028069 A1 | 2/2018 | Shi et al. |
| 2018/0028070 A1 | 2/2018 | Shi |
| 2018/0028071 A1 | 2/2018 | Shi |
| 2018/0028072 A1 | 2/2018 | Shi |
| 2018/0110768 A1 | 4/2018 | Quik et al. |
| 2018/0110975 A1 | 4/2018 | Ivanoff et al. |
| 2018/0165566 A1 | 6/2018 | Rogers et al. |
| 2018/0168504 A1 | 6/2018 | Ding et al. |
| 2018/0197637 A1 | 7/2018 | Chowdhury |
| 2018/0374381 A1 | 12/2018 | Darmour et al. |
| 2019/0000828 A1 | 1/2019 | Azhir |
| 2019/0009019 A1* | 1/2019 | Shor .................. A61M 5/1782 |
| 2019/0054078 A1 | 2/2019 | Azhir et al. |
| 2019/0054235 A1 | 2/2019 | DiPierro et al. |
| 2019/0231707 A1 | 8/2019 | Stiles et al. |
| 2019/0275308 A1 | 9/2019 | Netzel et al. |
| 2019/0336738 A1 | 11/2019 | Johnson et al. |
| 2019/0374482 A1 | 12/2019 | Schaller et al. |
| 2020/0030590 A1 | 1/2020 | Buchman et al. |
| 2020/0330369 A1 | 10/2020 | DiPierro |
| 2020/0368175 A1 | 11/2020 | Arora et al. |
| 2021/0169822 A1 | 6/2021 | Zumbrunn et al. |
| 2021/0196935 A1 | 7/2021 | Tong et al. |
| 2024/0408362 A1 | 12/2024 | Johnston et al. |
| 2024/0416095 A1 | 12/2024 | Tong et al. |
| 2024/0424270 A1 | 12/2024 | Netzel et al. |

FOREIGN PATENT DOCUMENTS

| | | | |
|---|---|---|---|
| CA | 2142871 A1 | 3/1994 | |
| CN | 1704056 A | 12/2005 | |
| DE | 19958554 A1 | 1/2001 | |
| DE | 10105759 C1 | 10/2001 | |
| DE | 10103158 A1 | 8/2002 | |
| EP | 311313 A2 | 4/1989 | |
| EP | 0314528 B1 | 12/1992 | |
| EP | 0354554 B1 | 1/1994 | |
| EP | 0726005 A1 | 8/1996 | |
| EP | 857725 A1 | 8/1998 | |
| EP | 870768 A1 | 10/1998 | |
| EP | 955301 A2 | 11/1999 | |
| EP | 0612525 B1 | 9/2001 | |
| EP | 1815784 A1 | 8/2007 | |
| EP | 1977746 B1 | 7/2014 | |
| EP | 1662989 B1 | 9/2014 | |
| EP | 3016586 A2 | 5/2016 | |
| GB | 1528391 A | 10/1978 | |
| GB | 2030862 A | 4/1980 | |
| GB | 2142822 A | 1/1985 | |
| GB | 2230439 A | 10/1990 | |
| JP | 02202813 A | 8/1990 | |
| JP | H09504974 A | 5/1997 | |
| JP | 09512006 A | 12/1997 | |
| JP | 2000515394 A | 11/2000 | |
| JP | 2001505491 A | 4/2001 | |
| JP | 2002092180 A | 3/2002 | |
| JP | 2003506477 A | 2/2003 | |
| JP | 2005521526 A | 7/2005 | |
| JP | 2005525147 A | 8/2005 | |
| JP | 2007509661 A | 4/2007 | |
| JP | 2008523918 A | 7/2008 | |
| JP | 2009544338 A | 12/2009 | |
| JP | 2010/507457 | 3/2010 | |
| JP | 2010518914 A | 6/2010 | |
| JP | 2010279808 A | 12/2010 | |
| JP | 2011036491 A | 2/2011 | |
| JP | 2013524951 A | 6/2013 | |
| JP | 2015070868 A | 4/2015 | |
| JP | 2016202904 A | 12/2016 | |
| KR | 20180011653 A * | 2/2018 | ........ A61M 37/0015 |
| WO | WO86/07269 A1 | 12/1986 | |
| WO | WO88/003803 A1 | 6/1988 | |
| WO | WO91/14441 A1 | 10/1991 | |
| WO | WO92/021339 A1 | 12/1992 | |
| WO | WO94/008992 A1 | 4/1994 | |
| WO | WO94/010987 A1 | 5/1994 | |
| WO | WO95/06497 A1 | 3/1995 | |
| WO | WO96/015123 A1 | 5/1996 | |
| WO | WO96/040682 A1 | 12/1996 | |
| WO | WO97/011072 A1 | 3/1997 | |
| WO | WO97/011073 A1 | 3/1997 | |
| WO | WO97/11741 A1 | 4/1997 | |
| WO | WO97/18782 A1 | 5/1997 | |
| WO | WO97/019059 A1 | 5/1997 | |
| WO | WO97/028801 A1 | 8/1997 | |
| WO | WO97/034605 A1 | 9/1997 | |
| WO | WO97/042941 A2 | 11/1997 | |
| WO | WO97/046554 A1 | 12/1997 | |
| WO | WO98/042713 A1 | 10/1998 | |
| WO | WO98/46093 A1 | 10/1998 | |
| WO | WO98/054152 A1 | 12/1998 | |
| WO | WO98/054181 A1 | 12/1998 | |
| WO | WO98/054182 A1 | 12/1998 | |
| WO | WO98/054189 A1 | 12/1998 | |
| WO | WO98/55107 A1 | 12/1998 | |
| WO | WO99/002517 A1 | 1/1999 | |
| WO | WO99/003859 A1 | 1/1999 | |
| WO | WO99/021834 A1 | 5/1999 | |
| WO | WO99/024422 A1 | 5/1999 | |
| WO | WO99/066916 A1 | 12/1999 | |
| WO | WO00/010997 A1 | 3/2000 | |
| WO | WO00/032600 A1 | 6/2000 | |

(56) References Cited

FOREIGN PATENT DOCUMENTS

| | | |
|---|---|---|
| WO | WO00/034279 A1 | 6/2000 |
| WO | WO00/034284 A1 | 6/2000 |
| WO | WO00/035279 A1 | 6/2000 |
| WO | WO00/035456 A1 | 6/2000 |
| WO | WO00/044755 A1 | 8/2000 |
| WO | WO00/064885 A1 | 11/2000 |
| WO | WO00/066596 A1 | 11/2000 |
| WO | WO00/74763 A2 | 12/2000 |
| WO | WO00/74933 A1 | 12/2000 |
| WO | WO01/005459 A1 | 1/2001 |
| WO | WO01/037814 A1 | 5/2001 |
| WO | WO02/076211 A1 | 10/2002 |
| WO | WO03/022349 A2 | 3/2003 |
| WO | WO03/026655 A1 | 4/2003 |
| WO | WO03/055486 A1 | 7/2003 |
| WO | WO03/061656 A1 | 7/2003 |
| WO | WO03/070191 A1 | 8/2003 |
| WO | WO03/097146 A1 | 11/2003 |
| WO | WO2004/024124 A1 | 3/2004 |
| WO | WO2004/073429 A1 | 9/2004 |
| WO | WO2005/023227 A2 | 3/2005 |
| WO | WO2005/079161 A2 | 9/2005 |
| WO | WO2006/069097 A2 | 6/2006 |
| WO | WO2007/013975 A2 | 2/2007 |
| WO | WO2007/041544 A1 | 4/2007 |
| WO | WO2007/104574 A2 | 9/2007 |
| WO | WO2007/104575 A2 | 9/2007 |
| WO | WO2007/133141 A1 | 11/2007 |
| WO | WO2008/024408 A2 | 2/2008 |
| WO | WO2008/054788 A2 | 5/2008 |
| WO | WO2008/069921 A2 | 6/2008 |
| WO | WO2008/069970 A2 | 6/2008 |
| WO | WO2008/069972 A2 | 6/2008 |
| WO | WO2008/122049 A2 | 10/2008 |
| WO | WO2008/135283 A1 | 11/2008 |
| WO | WO2009/136304 A2 | 11/2009 |
| WO | WO2011/088072 A2 | 7/2011 |
| WO | WO2012/012846 A1 | 2/2012 |
| WO | WO2012/101060 A1 | 8/2012 |
| WO | WO2013/093666 A1 | 6/2013 |
| WO | WO2013/168068 A1 | 11/2013 |
| WO | WO2014/001877 A1 | 1/2014 |
| WO | WO2014/043502 A1 | 3/2014 |
| WO | WO2016/081616 A2 | 5/2016 |
| WO | WO2016/132368 A1 | 8/2016 |
| WO | WO2016/161416 A1 | 10/2016 |
| WO | WO2017/053938 A1 | 3/2017 |
| WO | WO2017/125455 A1 | 7/2017 |
| WO | WO2018/026759 A1 | 2/2018 |
| WO | WO2018/129363 A1 | 7/2018 |
| WO | WO2018/133786 A1 | 7/2018 |
| WO | WO2019/090125 A2 | 5/2019 |
| WO | WO2019/232077 A1 | 12/2019 |

OTHER PUBLICATIONS

Ahlskog et al.; Frequency of levodopa-related dyskinesias and motor fluctuations as estimated from the cumulative literature; Movement Disorders; 16(3); pp. 448-458; May 1, 2001.
Angulo et al.; Oral nicotine in treatment of primary sclerosing cholangitis: a pilot study; Digestive diseases and sciences; 44(3); pp. 602-607; Mar. 1, 1999.
Azhir, Arasteh; U.S. Appl. No. 62/320,871 entitled "Compositions and methods for treatment related to fall and fall frequency in neurodegenerative diseases", filed Apr. 11, 2016.
Baldessarini et al.; Preclinical studies of the pharmacology of aporphines; In: Gessa GL, Corsini GU, eds.; Apomorphine and other dopaminomi-'metics vol. 1, Basic pharmacology; New York: Raven Press; pp. 219-228; (year of pub. sufficiently earlier than effective US filing date and any foreign priority date) 1981.
Balfour et al.; Pharmacology of nicotine and its therapeutic use in smoking cessation and neurodegenerative disorders; Pharmacology and Therapeutics; 72(1); pp. 51-81; Jan. 1, 1996.

Benowitz et al.; Sources of variability in nicotine and cotinine levels with use of nicotine nasal spray, transdermal nicotine, and cigarette smoking; British Journal of Clinical Pharmacology; 43(3); pp. 259-267; Mar. 1, 1997.
Benowitz et al.; Stable isotope studies of nicotine kinetics and bioavailability; Clin Pharm and Ther; 49(3); pp. 270-277; Mar. 1991.
Bordia et al.; Continuous and intermittent nicotine treatment reduces L-3 4-dihydroxyphenyalanine (L-DOPA)-induced dyskinesias in rat model of Parkinson's diseases; Journal of Pharmacology ans Experimental Therapeutics; 327(1); pp. 239-247; Oct. 1, 2008.
Bordia et al.; Partial recovery of striatal nicotinic receptors in l-methyl-4-phenyl-1,2,3,6-tetrahydropyridine (MPTP)-lesioned monkeys with chronic oral nicotinic; The Journal of Pharmacology and Experimental Therapeutics; 319(1); pp. 285-292; Oct. 1, 2006.
Bove et al.; Toxin-induced models of Parkinson's disease; NeuroRx; 2(3); pp. 484-494; Jul. 31, 2005.
Bricker et al.; Randomized controlled pilot trial of a smartphone app for smoking cessation using acceptance and commitment therapy: Drug and Alcohol Dependence; 143; pp. 87-94; Oct. 1, 2014 (Author Manuscript).
Brotchie et al.; Levodopa-induced dyskinesia in Parkinson's disease; Journal of Neural Transmission; 112(3); pp. 359-391; Mar. 1, 2005.
Bruguerolle; Chronopharmacokinetics; Clin Pharmacokinet; 35(2); pp. 83-94; Aug. 1998.
Calabresi et al.; Levodopa-induced dyskinesias inpatients with parkinson's disease: filling the bench-to-bedside gap; The Lancet Neurology; 9(11); pp. 1106-1117; Nov. 1, 2010.
Carta et al.; Role of striatal L-DOPA in the production of dyskinesia in 6-hydroxydopamine lesioned rats; Journal of Neurochemistry; 96(6); pp. 1718-1727; Mar. 2006.
Chen et al.; Enhanced striatal opioid receptor-mediated G-protein activation in L-DOPA-treated dyskinetic monkeys; Neuroscience; 132(2); pp. 409-420; Dec. 31, 2005.
Damaj et al.; Antinociceptive responses to nicotinic acetylcholine receptor ligands affer systemic and intrathecal administration in mice; Journal of Pharmacology and Experimental Therapeutics; 284(3); pp. 1058-1065; Mar. 1, 1998.
Davie; A review of Parkinson's disease. British Medical Bulletin 2008 86(1): 109-127; Apr. 8, 2008.
De La Fuente et al.; The placebo effect in Parkinson's disease; Trends in Neuroscience; 25(6); pp. 302-306; Jun. 1, 2002.
Di Monte et al.; Relationship among nigrostriatal denervation, parkinsonism, and dyskinesias in the MPTP primate model; Movement Disorders; 15(3); pp. 459-466; May 1, 2000.
Dockser-Marcus, A.; New research shows drugs work best at certain times; The Wall Street Journal; 6 pgs.; May 27, 2003; (http://www.wsj.com/articles/SB1053973124865087000).
Domino et al.; Nicotine alone and in combination with L-DOPA methyl ester or the D(2) agonist N-0923 in MPTP-induced chronic hemiparkinsonian monkeys; Exp Neurol; 158(2); pp. 414-421; Aug. 1999.
Dutil; Benzoyl Peroxide: Enhancing antibiotic efficacy in acne management; Skin Therapy Letter; 15(1); pp. 5-7; Nov./Dec. 2010.
Ebersbach et al.; Worsening of motor performance in patients with Parkinson's disease following transdermal nicotine administration; Movement Disorders; 14(6); pp. 1011-1013; Nov. 1, 1999.
Ethicon Endo-Surgery, Inc.; Sedasys® Computer-assisted personalized sedation system essential product information; retrieved May 12, 2015 from the internet (http://www.sedasys.com/explore-the-system/essential-product-information); 2 pgs.
Fagerstrom et al.; Nicotine may relieve symptoms of Parkinson's disease; Psychopharmacology; 116(1); pp. 117-119; Sep. 16, 1994.
Food and Drug Administration; Guidance for Industry—Dissolution Testing of Immediate Release Solid Oral Dosage Forms; 17 pages; retrieved from the internet (https://www.fda.gov/downloads/drugs/guidances/ucm070237.pdf); Aug. 1997.
Gatto et al.; TC-1734: An orally active neuronal nicotinic acetylcholine receptor modulator with antidepressant, neuroprotective and long-lasting cognitive effects; CNS Drug Reviews; 10(2); pp. 147-166; Jun. 1, 2004.

(56) References Cited

OTHER PUBLICATIONS

Gennaro (Editor); Remington: The Science and Practice of Pharmacy; 19th Ed.; Mack Publishing Co.; Easton, PA; p. 1582-1584; Jun. 1995.
Giannos; Chapter 20: Pulsatile fSmartf Drug Delivery, in Skin Delivery Systems: Transdermals, Dermatologicals, and Cosmetic Actives; (ed.) Wille, Jr; Blackwell Pub.; Oxford, UK; pp. 327-357; Jun. 2006.
Gora; Nicotine transdermal systems; The Annals of Pharmacotherapy; 27(6); pp. 742-750; Jun. 1993.
Gotti et al.; Brain nicotinic acetylcholine receptors: native subtypes and their relevance; Treands in Pharmacological Sciences; 27(9); pp. 482-491; Sep. 30, 2006.
Green et al.; An oral formulation of nicotine for release and absorption in the colon: its development and pharmacokinetics. British Journal of Clinical Pharmacology; 48(4); pp. 485-493; Oct. 1999.
Gries et al.; Importance of Chronopharmacokinetics in Design and Evaluation of Transdermal Drug Delivery Systems; J Pharmaocol Exp Ther; 285(2); pp. 457-463; May 1998.
Guy; Current status and future prospects of transdermal drug delivery; Pharm Res; 13(12); pp. 1765-1769; Dec. 1996.
Halberg et al.; Chronomics: circadian and circaseptan timing of radiotherapy, drugs, calories, perhaps nutriceuticals and beyond; Journal of Experimental Therapeutics and Oncology; 3(5); pp. 223-260; Sep. 2003.
He et al.; Autoradiographic analysis of dopamine receptor-stimulated [35S]GTPtS binding in rat striatum; Brain Research; 885(1); pp. 133-136; Dec. 1, 2000.
He et al; Autoradiographic analysis of N-methyl-D-aspartate receptor binding in monkey brain: Effects of l-methyl-4-phenyl-1,2,3,6-tetrahydropyridine andlevodopa treatment; Neuroscience; 99(4); pp. 697-704; Aug. 23, 2000.
Heffner et al.; Feature-level analysis of a novel smartphone applicationn for smoking cessation; Am. J. Drug Alcohol Abuse; 41(1); pp. 68-73; Jan. 2015 (Author Manuscript).
Hrushesky; Temporally optimizable delivery systems: sine qua non for the next therapeutic revolution; J Cont Rel; 19(1-3); pp. 363-368; Mar. 1992.
Hsu et al.; Effect of the D3 dopamine receptor partial agonist BP897 [N-[4-(4-(2-methoxyphenyl)piperazinyl)butyl]-2-napthamide] on L-3,4-dihydroxyphenylalanine-induced dyskinesias and parkinsonism in squirrel monkeys; The Journal of Pharmacology and Experimental Therapeutics. 311(2); pp. 770-777; Nov. 1, 2004.
Huang et al.; Inhibitory effects of curcumin on in vitro lipoxygenase and cyclooxygenase activities in mouse epidermis; Cancer Res; 51(3); pp. 813-819; Feb. 1991.
Hukkanen et al.; Metabolism and disposition kinetics of nicotine; Pharmacological Reviews; 57(1); pp. 79-115; Mar. 1, 2005.
Hurley; Growing list of positive effects of nicotine seen in neurodegenerative disorders; Neurology Today; 12(2); pp. 37-38; Jan. 19, 2012.
Ingram et al.; Preliminary observations of oral nicotine therapy for inflammatory bowel disease: an open-label phase I-II study of tolerance; Inflamm Bowel Diseases; 11(12); pp. 1092-1096; Dec. 1, 2005.
Janson et al.; Chronic nicotine treatment counteracts dopamine D2 receptor upregulation induced by a partial meso-diencephalic hemitransection in the rat; Brain Res.; 655(1-2); pp. 25-32; Aug. 29, 1994.
Jarvik et al.; Inhibition of cigarette smoking by orally administered nicotine; Clinical Pharmacology and Therapeutics; 11(4); pp. 574-576; Jul. 1, 1970.
Jeyarasasingam et al.; Nitric oxide is involved in acetylcholinesterase inhibitor-induced myopathy in rats; The Journal of Pharmacology and Experimental Therapeutics; 295(1); pp. 314-320; Oct. 1, 2000.
Jeyarasasingam et al.; Stimulation of non-o7 nicotinic receptors partially protects dopaminergic neurons from l-methyl-4-phenylpyridinium-induced toxicity in culture; Neuroscience; 109(2); pp. 275-285; Jan. 28, 2002.
Jeyarasasingam et al.; Tacrine, a reversible acetylcholinesterase inhibitor, induces myopathy; Neuroreport; 11(6); pp. 1173-1176; Apr. 27, 2000.
Kalish et al.; Prevention of contact hypersensitivity to topically applied drugs by ethacrynic acid: potential application to transdermal drug delivery; J. Controll Rel; 48(1); pp. 79-87; Sep. 1997.
Kalish et al.; Sensitization of mice to topically applied drugs: albuterol, chlorpheniramine, clonidine and nadolol; Contact Dermatitis; 35(2); pp. 76-82; Aug. 1996.
Kelton et al.; The effects of nicotine on Parkinson's disease; Brain Cognition; 43(1-3); pp. 274-282; Jun. 2000.
Kennelly; Microcontrollers drive home drug delivery; 3 pgs; posted Jul. 2014; (retrieved Jul. 26, 2016 from the internet: http://electronicsmaker.com/microcontrollers-drive-home-drug-delivery-2.
Kiwi Drug; Buy nicorette microtabs; 3 pages; retrieved from the internet (www.kiwidrug.com/search/nicorette_microtabs); on Jul. 26, 2018.
Kotwal; Enhancement of intophoretic transport of diphenhydramine hydrochloride thermosensitive gel by optimization of pH, polymer concentration, electrode design, and pulse rate; AAPS PharmSciTech; 8(4); pp. 320-325; Oct. 2007.
Kulak et al.; 5-Iodo-A-85380 binds to oconotoxin Mil-sensitive nicotinic acetylcholine receptors (nAChRs) as well as o4j32* subtypes; Journal of Neurochemistry; 81(2); pp. 403-406; Apr. 1, 2002.
Kulak et al.; Declines in different pi* nicotinic receptor populations in monkey striatum after nigrostriatal damage; The Journal of Pharmacology and Experimental Therapeutics; 303(2); pp. 633-639; Nov. 1, 2002.
Kulak et al.; Loss of nicotinic receptors in monkey striatum after l-methyl-4-phenyl-1,2,3,6-tetrahydropyridine treatment is due to a decline in oconotoxin Mil sites; Molecular Pharmacology; 61(1); pp. 230-238; Jan. 1, 2002.
Kumar et al.; Levodopa-dyskinesia incidence by age of Parkinson's disease onset; Movement disorders; 20(3); pp. 342-344; Mar. 2005.
Kydonieus et al. (Editors); Biochemical Modulation of Skin Reactions; CRC Press; Boca Ratan, FL; pp. 9-10; Dec. 1999.
Labrecque, G. et al.; Chronopharmacokinetics; Pharmaceutical News; 4(2); pp. 17-21; (year of pub. sufficiently earlier than effective US filing date and any foreign priority date) 1997.
Lai et al.; Long-term nicotine treatment decreases striatal a6* nicotinic acetylcholine receptor sites and function in mice; Molecular Pharmacology; 67(5); pp. 1639-1647; May 1, 2005.
Lai et al.; Selective recovery of striatal 1251-a-conotoxinMII nicotinic receptors after nigrostriatal damage in monkeys; Neuroscience; 127(2); pp. 399-408; Dec. 31, 2004.
Lamberg; Chronotherapeutics: Implications for drug therapy; American Pharmacy; NS31(11); pp. 20-23; Nov. 1991.
Langston et al.; Investigating levodopa-induced dyskinesias in the parkinsonian primate; Annals of Neurology; 47(4 Suppl 1); pp. S79-S88; Apr. 2000.
Laser et al.; A review of micropumps; J. of Micromech. And Microeng.; 14; pp. R35-R64; Apr. 2004.
Lee et al.; A comprehensive review of opioid-induced hyperalgesia; Pain Physician; 14; pp. 145-161; Mar. 2011.
Lemay et al.; Lack of efficacy of a nicotine transdermal treatment on motor and cognitive deficits in Parkinson's disease; Prog Neuropsychopharmacol Biol Psychiatry; 28(1); pp. 31-39; Jan. 2004.
Lemmer; Clinical Chronopharmacology: The Importance of Time in Drug Treatment, in Ciba Foundation Symposium 183—Circadian Clocks and their Adjustment (eds. Chadwick and Ackrill); John Wiley & Sons, Inc.; pp. 235-253; Apr. 1995.
Lemmer; Implications of chronopharmacokinetics for drug delivery: antiasthmatics, H2-blockers and cardiovascular active drugs; Adv Drug Del Rev; 6(1); pp. 83-100; Jan./Feb. 1991.
Lemmer; The clinical relevance of chronopharmacology in therapeutics; Pharmacological Research; 33(2); pp. 107-115; Feb. 1996.
LeWitt et al.; New developments in levodopa therapy; Neurology; 62(No. 1, Suppl. 1); pp. S9-S16; Jan. 2004.
Lieber Man; Compressed tablets by direct compression; Pharmaceutical Dosage forms; vol. 1, 2nd ed.; Marcel Dekker Inc.; pp.

(56) References Cited

OTHER PUBLICATIONS 195-246; (year of pub. sufficiently earlier than effective US filing date and any foreign priority date) 1989.
Lieberman; Compression—coated and layer tablets; Pharmaceutical Dosage forms; vol. 1, 2nd ed.; Marcel Dekker Inc.; pp. 266-271; (year of pub. sufficiently earlier than effective US filing date and any foreign priority date) 1989.
Lundblad et al.; Cellular and behavioural effects of the adenosine A2a receptor antagonist KW-6002 in a rat model of l-DOPA-induces Dyskinesia; Journal of Neurochemistry; 84(6); pp. 1398-1410; Mar. 2003.
Madandla et al,; Voluntary running provides neuroprotection in rats after 6-hydroxydopamine injection into the medial forebrain bundle; Metabolic Brain Disease; 19(1-2); pp. 43-50; Jun. 2004.
Maillefer et al.; A high-performance silicon micropump for an implantable drug delivery system; 12th IEEE Int'l Conf. on Micro Electro Mechanical Systems; MEMS '99; Orlando, FL; pp. 541-546; Jan. 1999.
Matta et al.; Guidelines on nicotine dose selection for in vivo research; Psychopharmacology (Berl.); 190(3); pp. 269-319; Feb. 1, 2007.
Mccallum et al,; Decrease in alpha3*/alpha6* nicotinic receptors in monkey brain after nigrostriatal damage; Molecular Pharmacology; 68(3); pp. 737-746; Sep. 2005.
Mccallum et al.; Compensation in pre-synaptic dopaminergic function following nigrostriatal damage in primates; Journal of Neurochemistry; 96(4); pp. 960-972; Feb. 1, 2006.
Mccallum et al.; Differential regulation of mesolimbic alpha 3/alpha 6 beta 2 and aplha 4 beta 2 nicotinic acetylcholine receptor sites and function after long-term oral nicotine to monkeys; The Journal of Pharmacology and Experimental Therapeutics; 318(1); pp. 381-388; Jul. 2006.
Mccallum et al.; Increases in aplha 4* but not aplha3*/alpha6* nicotinic receptor sites and function in the primate striatum following chronic oral nicotine treatment; Journal of Neurochemistry; 96(4); pp. 1028-1041; Feb. 2006.
McNeil Sweden AB. Package Leaflet: Information for the user. Nicorette Microtab Lemon 2mg sublingual tablets. (This leaflet was last approved in Apr. 16, 2008). retrived from ( www.lakemedelsverket.se/SPC_PIL/Pdf/enhumpil/Nicorette%20Microtab%20Lemon%202mg%20sublingual%20tablet%20ENG.pdf.) Accessed Aug. 19, 2010.
Medtronic; MiniMed Paradigm® Veo(TM) System (product info.); retrieved May 12, 2015 from the internet: (http://www.medtronic.co.uk/your-health/diabetes/device/insulin-pumps/paradigm-veo-pump/); 3 pgs.
Meissner et al.; Priorities in parkinson's disease research; Nature reviews Drug Discovery; 10(5); pp. 377-393; May 1, 2011.
Menzaghi et al.; Interactions between a novel cholinergic ion channel against, SIB-1765F anf L-DOPA in the reserpine model of parkinson's disease in rats; Journal of Pharmacology and Experimental Therapeutics; 280(1); pp. 393-401; Jan. 1, 1997.
Merck manual of therapy and diagnosis; 17th edition. Merck Research Laboratories; pp. 1466-1471; (year of pub. sufficiently earlier than effective US filing date and any foreign priority date) 1999.
Meredith et al.; Behavioral models of Parkinson's disease in rodents: a new look at an old problem; Movement Disorders; 21(10); pp. 1595-1606; Oct. 1, 2006.
Meshul et al.; Nicotine Affects Striatal Glutamatergic Function in 6-OHDA Lesioned Rats; Advanced in behavioural Biology, Basal Ganglia VI.; Springer, Boston, MA.; vol. 54; pp. 589-598; (year of pub. sufficiently earlier than effective US filing date and any foreign priority date) 2002.
Meshul et al.; Nicotine alters striatal glutamate function and decreases the apomorphine-induced contralateral rotations in 6-OHDA-lesioned rats; Experimental Neurology; 175(1); pp. 257-274; May 31, 2002.
Molander et al.; Reduction of tobacco withdrawal symptoms with a sublingual nicotine tablet: A placebo controlled study; Nictonie & Tob. Res.; 2(2); pp. 187-191; May 2000.
Murphy et al.; Transdermal drug delivery systems and skin sensitivity reactions. Incidence and management; Am. J. Clin Dermatol.; 1(6); pp. 361-368; Nov./Dec. 2000.
Mutalik et al.; Glibenclamide transdermal patches: physicochemical, pharmacodynamic, and pharmacokinetic evaluation; J Pharm Sci; 93(6); pp. 1577-1594; Jun. 2004.
Mutalik et al.; Glipizide matrix transdermal systems for diabetes mellitus: preparation, in vitro and preclinical studies; Life Sci; 79(16; pp. 1568-1567; Sep. 2006.
Nakadate et al.; Effects of chalcone derivatives on lipoxygenase and cyclooxygenase activities of mouse epidermis; Prostaglandins; 30(3); pp. 357-368; Sep. 1985.
National Institute of Neurological Disorders and Stroke. Parkinson's Disease: Hope Through Research. 54 pages; Retrieved from the internet (https://catalog.ninds.nih.gov/pubstatic//15-139/15-139.pdf) on Jan. 15, 2018.
Newhouse et al.; Nicotine treatment of mild cognitive impairment: a 6-month double-blind pilot clinical trial; Neurology; 78(2); pp. 91-101; Jan. 10, 2012.
Newmark; Plant phenolics as potential cancer prevention agents; Chapter 3 in Dietary Phytochemicals in Cancer Prevention; Chap. 3; Adv. Exp. Med. Biol. 401; pp. 25-34; © 1996.
Ohdo; Changes in toxicity and effectiveness with timing of drug administration: implications for drug safety; Drug Safety; 26(14); pp. 999-1010; Dec. 2003.
Olanow; The scientific basis for the current treatment of Parkinson's disease; Annu. Rev. Med.; 55; pp. 41-60; Feb. 18, 2004.
Olsson et al.; A valve-less planar pump in silicon; IEEE; The 8th International Conference on Solid-State Sensors and Actuators; vol. 2; pp. 291-294, Jun. 1995.
Olsson et al.; An improved valve-less pump fabricated using deep reactive ion etching; Proc. Of the IEEE, 9th Int'l Workshop on MEMS; San Diego, CA; pp. 479-484; Feb. 11-15, 1996.
O'Neill et al.; The role of neuronal nicotinic acetylcholine receptors in acute and chronic neurodegeneration; Current Drug Targets—CNS and Neurological Disorders; 1(4); pp. 399-412; Aug. 1, 2002.
Parkinson Study Group; Levodopa and the progression of Parkinson's disease; N Engl J Med.; 351; pp. 2498-2508; Dec. 9, 2004.
Petzinger et al.; Reliability and validity of a new global dyskinesia rating scale in the MPTP-lesioned non-human primate; Movement Disorders; 16(2); pp. 202-207; Mar. 1, 2001.
Priano et al.; Nocturnal anomalous movement reduction and sleep microstructure analysis in parkinsonian patients during 1-night transdermal apomorphine treatment; Neurol Sci.; 24(3); pp. 207-208; Oct. 2003.
Prosise et al.; Effect of abstinence from smoking on sleep and daytime sleepiness; Chest; 105(4); pp. 1136-1141; Apr. 1994.
Quik et al.; Chronic oral nicotine normalizes dopaminergic function and synaptic plasticity in l-methyl-4-phenyl-1,2,3,6-tetrahydropyridine-lesioned primates; The Journal of Neuroscience; 26(17); pp. 4681-4689; Apr. 26, 2006.
Quik et al.; Chronic oral nicotine treatment protects against striatal degeneration in MPTP-treated primates; Journal of Neurochemistry; 98(6); pp. 1866-1875; Sep. 1, 2006.
Quik et al.; Differential alterations in nicotinic receptor a6 and /33 subunit messenger RNAs in monkey substantia nigra after nigrostriatal degeneration; Neuroscience; 100(1); pp. 63-72; Sep. 7, 2000.
Quik et al.; Differential declines in striatal nicotinic receptor subtype function after nigrostriatal damage in mice; Molecular Pharmacology; 63(5); pp. 1169-1179; May 1, 2003.
Quik et al.; Differential nicotinic receptor expression in monkey basal ganglia; Effects of nigrostriatal damage; Neuroscience; 112(3); pp. 619-630; Jul. 5, 2002.
Quik et al.; Expression of D3 receptor messenger RNA and binding sites in monkey striatum and substantia nigra after nigrostriatal degeneration; Effect of levodopa treatment.;Neuroscience; 98(2); pp. 263-273; Jun. 30, 2000.

(56) References Cited

OTHER PUBLICATIONS

Quik et al.; Increases in striatal preproenkephalin gene expression are associated with nigrostriatal damage but not L-DOPA-induced dyskinesias in the squirrel monkey; Neuroscience; 113(1); pp. 213-220; Aug. 2, 2002.

Quik et al.; L-DOPA treatment modulates nicotinic receptors in monkey striatum; Mol Pharmacol; 64(3); pp. 619-628; Sep. 2003.

Quik et al.; Localization of nicotinic receptor subunit mRNAs in monkey brain by in situ hybridization; The Journal of Comparative Neurology; 425(1); pp. 58-69; Sep. 11, 2000.

Quik et al.; Loss of a-conotoxinMII- and A85380-sensitive nicotinic receptors in Parkinson's disease striatum; Journal of Neurochemistry; 88(3); pp. 668-679; Feb. 1, 2004.

Quik et al.; Nicotine administration reduces striatal MPP+ levels in mice; Brain Research; 917(2); pp. 219-224; Nov. 2, 2001.

Quik et al.; Nicotine and nicotinic receptors; relevance to Parkinson's disease; Neurotoxicology; 23(4-5); pp. 581-594; Oct. 2002.

Quik et al.; Nicotine and Parkinson's disease: implications for therapy; Movement Disorders; 23(12); pp. 1641-1652; (Author Manuscript); Sep. 1, 2008.

Quik et al.; Nicotine as a potential neuroprotective agent for Parkinson's disease; Movement disorders; 27(8); pp. 947-957; Jul. 1, 2012.

Quik et al.; Nicotine neuroprotection against nigrostriatal damage: importance of the animal model; Trends in Pharmacological sciences; 28(5); pp. 229-235; May 31, 2007.

Quik et al.; Nicotine reduces levodopa-induced dyskinesias in lesioned monkeys; Annals of neurology; 62(6); pp. 588-596; (Author Manuscript); Dec. 1, 2007.

Quik et al.; Nicotinic receptors and Parkinson's disease; European Journal of Pharmacology; 393(1); pp. 223-230; Mar. 30, 2000.

Quik et al.; Striatal a6* nicotinic acetylcholine receptors: Potential targets for Parkinson's disease therapy; The Journal of Pharmacology and Experimental Therapeutics; 316(2); pp. 481-489; Feb. 1, 2006.

Quik et al.; Subunit composition of nicotinic receptors in monkey striatum: Effect of treatments with 1-methyl-4-phenyl-1,2,3,6-tetrahydropyridine or L-DOPA; Molecular Pharmacology; 67(1); pp. 32-41; Jan. 2005.

Quik et al.; Vulnerability of 125I-a-conotoxin Mil binding sites to nigrostriatal damage in monkey; The Journal of Neuroscience; 21(15); pp. 5494-5500; Aug. 1, 2001.

Quik; Smoking, nicotine and Parkinson's disease; Trends in Neurosciences; 27(9); pp. 561-568; Sep. 2004.

Redfern et al.; Circadian rhythms, jet lag, and chronobiotics: An overview; Chronobiology International; 11(4); pp. 253-265; Aug. 1994.

Reinberg; Concepts of Circadian Chronopharmacology; Annals of the New York Academy of Sciences; 618 (Temporal Control of Drug Delivery); pp. 102-115; Feb. 1991.

Rueter et al.; ABT-089: Pharmacological properties of a neuronal nicotinic acetylcholine receptor agonist for the potential treatment of cognitive disorders; CNS Drug Reviews; 10(2); pp. 167-182; Jun. 1, 2004.

Samii et al.; Parkinson's disease; The Lancet; 363(9423); pp. 1783-1793; May 29, 2004.

Savitt et al.; Diagnosis and treatment of Parkinson disease: molecules to medicine; The Journal of Clinical Investigation; 116(7); pp. 1744-1754; Jul. 3, 2006.

Schapira; Disease modification in Parkinson's disease; The Lancet Neurology; 3(6); pp. 362-368; Jun. 30, 2004.

Schneider et al.; Effects of SIB-1508Y, a novel neuronal nictonic acetylcholine receptor agonist, on motor behavior in parkinsonian monkeys; Movement Disorders; 13(4); pp. 637-642; Jul. 1, 1998.

Schneider et al.; Effects of the nicotinic acetylcholine receptor agonist SIB-1508Y on object retrieval performance in MPTP-treated monkeys: Comparison with levodopa treatment; Annals of Neurology; 43(3); pp. 311-317; Mar. 1, 1998.

Schober et al.; Classic toxin-induced animal models of Parkinson's disease: 6-OHDA and MPTP; Cell and Tissue Research; 318(1); pp. 215-224; Oct. 1, 2004.

Shin et al.; Enhanced bioavailability of triprolidine from the transdermal TPX matrix system in rabbits; Int. J. Pharm.; 234(1-2); pp. 67-73; Mar. 2002.

Silver et al.; Transdermal nicotine and haloperidol in Tourette's disorder: a double-blind placebo-controlled study; Journal of Clinical Psychiatry; 62(9); pp. 707-714; Sep. 1, 2001.

Singer et al.; Nightmares in patients with Alzheimer's disease caused by donepezil: Therapeutic effect depends on the time of intake; Nervenarzt; 76(9); pp. 1127-1129; Sep. 2005 (Article in German w/ Eng. Summary).

Star Micronics Co., Ltd; Prototype Diaphragm Micro Pump SDMP305 (specifications); retrieved May 12, 2015 from the internet archive as of Jul. 2006 (http://www.star-m.jp/eng/products/develop/de07.htm); 3 pgs.

Stocchi et al.; Motor fluctuations in levodopa treatment: clinical pharmacology; European Neurology; 36(Suppl 1); pp. 38-42; Jan. 1996.

Strong et al.; Genotype and smoking history affect risk of levodopa-induced dyskinesias in parkinson's disease; Movement Disorders; 21(5); pp. 654-659; May 1, 2006.

Thiele et al. (Ed.); Oxidants and Antioxidants in Cutaneous Biology: Current Problems in Dermatology (Book 29); S. Karger; 196 pgs., Feb. 2001.

Togasaki et al.; Dyskinesias in normal squirrel monkeys induced by nomifensine and levodopa; Neuropharmacology; 48(3); pp. 398-405; Mar. 31, 2005.

Togasaki et al., Levodopa induces dyskinesias in normal squirrel monkeys; Annals of Neurology; 50(2); pp. 254-257; Aug. 1, 2001.

Togasaki et al.; The Webcam system: A simple, automated, computer-based video system for quantitative measurement of movement of nonhuman primates; Journal of Neuroscience Methods; 145(1); pp. 159-166; Jun. 30, 2005.

Tolosa et al.; Antagonism by piperidine of levodopa effects in Parkinson disease; Neurology; 27(9); pp. 875-877; Sep. 1, 1977.

U.S. Department of Health and Human Services, Food and Drug Administration, Center for Drug Evaluation and Research (CDER); Guidance for industry: Abuse-deterrent opioids—Evaluation and labeling; 24 pages; retrieved from the internet (http://www.fda.gov/downloads/drugs/guidancecomplainceregulatoryinformation/guidances/ucm344743.pdf); Jan. 2013.

United States of America VA/DoD; Tapering and discontinuing opioids; 2 pages; retrieved from the internet (http://www.healthquality.va.gov/guidelines/Pain/cot/OpioidTaperingFactSheet23May2013v1.pdf); on Sep. 1, 2016.

Vieregge et al.; Transdermal nicotine in PD: A randomized, double-blind, placebo-controlled study; Neurology; 57(6); pp. 1032-1035; Sep. 25, 2001.

Villafane et al.; Long-term nicotine administration can improve Parkinson's disease: report of a case after three years of treatment; Revista Neurologica Argentina; 27(2); pp. 95-97; (year of pub. sufficiently earlier than effective US filing date and any foreign priority date) 2002.

Warburton et al.; Facilitation of learning and state dependency with nicotine; Psychoparmacology; 89(1); pp. 55-59; May 1, 1986.

Wermuth et al.; Glossary of terms used in medicinal chemistry Pure & Appl. Chem., vol. 70(5); 1129-1143; 1998 AC recommendations 1998); Pure and Applied Chemistry; 70(5); pp. 1129-1143; Jan. 1998.

Wesnes et al.; Effects of scopolamine and nicotine on human rapid information processing performance; Psychoparmacology; 82(3); pp. 147-150; Sep. 1, 1984.

Westman et al.; Oral nicotine solution for smoking cessation: a pilot tolerability study; Nicotine and Tobacco Research; 3(4); pp. 391-396; Nov. 1, 2001.

Wille et al.; cis-urocanic Acid Induces Mast Cell Degranulation and Release of Preformed TNF-alpha: A Possible Mechanism Linking UVB and cis-urocanic Acid to Immunosuppression of Contact Hypersensitivity; Skin Pharm Appl Skin Physiol; 12(1-2); pp. 18-27; Jan. 1999.

(56) References Cited

OTHER PUBLICATIONS

Wille et al.; Inhibition of irritation and contact hypersensitivity by ethacrynic acid; Skin Pharm Appl Skin Physiol; 11(4-5); pp. 279-288; Jul. 1998.
Wille et al.; Inhibition of Irritation and Contact Hypersensitivity by Phenoxyacetic Acid Methyl Ester in Mice; Skin Pharm Appl Skin Physiol; 13(2); pp. 65-74; Mar. 2000.
Wille et al.; Several different ion channel modulators abrogate contact hypersensitivity in mice; Skin Pharm Appl Skin Physiol; 12(1-2); pp. 12-17; Jan. 1999.
Wille, J.; Novel topical delivery system for plant derived hydrophobic anti-irritant active (presentation abstract No. 273); 226th ACS National Meeting; New York, NY; Sep. 7-11, 2003.
Wille; In Closing: an editorial on Plant-Derived Anti-irritants. Cosmetics & Toiletries, 118 (8), Aug. 2003.
Wille; Novel plant-derived anti-irritants; (presented Dec. 5-6, 2002 at the 2002 Ann. Scientific Mtg. & Tech. Showcase); J. Cosmet. Sci.; 54; pp. 106-107; Jan./Feb. 2003.
Wille; Thixogel: Novel topical delivery system for hydrophobic plant actives; in Rosen (Ed.) Delivery System Handbook for Personal Care and Cosmetic Products; 1st Ed.; ISBN: 978-0-8155-1504-3; pp. 762-794; Sep. 2005.
Youan; Chronopharmaceutics: gimmick or clinically relevant approach to drug delivery?; J Cont Rel; 98(3); pp. 337-353; Aug. 2004.
Yun et al.; A distributed memory MIMD multi-computer with reconfigurable custom computing capabilities; IEEE; Proc. Int'l. Conf. on Parallel and Distributed Systems; pp. 8-13; Dec. 10-13, 1997.
Zubieta et al.; Placebo effects mediated by endogenous opioid activity on mu-opioid receptors; 25(34); pp. 7754-7762; Aug. 24, 2005.
Netzel et al.; U.S. Appl. No. 17/815,879 entitled "Drug Delivery methods and systems," filed Jul. 28, 2022.
Dipierro et al.; U.S. Appl. No. 17/936,750 entitled "Optimized bio-synchronous bioactive agent delivery system," filed Sep. 29, 2022.
Johnston et al.; U.S. Appl. No. 17/703,910 entitled "Transdermal drug delivery devices and methods," filed Mar. 24, 2022.
Tong et al.; U.S. Appl. No. 18/178,442 entitled "Drug Delivery methods and systems," filed Mar. 3, 2023.

\* cited by examiner

THERMALLY REGULATED TRANSDERMAL DRUG DELIVERY SYSTEM

CROSS REFERENCE TO RELATED APPLICATIONS

This application is a U.S. National Phase Application Under 35 U.S.C. § 371 of International Application No. PCT/US2019/061761, filed on Nov. 15, 2019, titled "THERMALLY REGULATED TRANSDERMAL DRUG DELIVERY SYSTEM," now International Publication No. WO 2020/102695, which claims priority to U.S. Provisional Application No. 62/768,768, filed on Nov. 16, 2018, titled "THERMALLY REGULATED TRANSDERMAL DRUG DELIVERY SYSTEM," each of which is herein incorporated by reference.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure is related generally to delivery of drugs and other active agents to a subject. More specifically, this disclosure relates to delivery of drugs and other active agents to skin or mucosa of a subject.

BACKGROUND

Cigarette smoking causes more than 480,000 deaths each year in the United States alone. Smoking increases the risk of coronary heart disease, stroke, lung cancer and other diseases up to 25 times. Despite the availability of pharmaceutical agents and various patches to help people stop smoking, many people are unable to give up smoking. This is mostly due to the strong cravings for smoking that smokers feel.

Further, approximately one million people in the United States alone have Parkinson's disease. Parkinson's disease is a degenerative disease of the nervous system with no known cure. The symptoms of Parkinson's disease include tremor, joint rigidity, balance problems, and slow movement. The symptoms get progressively worse over time.

Various systems have been developed to deliver pharmaceutical agents to a subject, such as those who wish to stop smoking or who suffer from Parkinson's disease. However, these existing systems suffer from various limitations and problems. For example, injections of a pharmaceutical drug is painful. Orally ingested drugs may not be available when needed and/or may dissolve in the acid of the stomach.

Transdermal drug delivery, i.e., using the skin of the body to deliver pharmaceutical agents, can be advantageous, as transdermal delivery prevents pharmaceutical agents from being digested in the stomach and eliminates pain from direct injection. However, the barrier function of the skin can make it difficult to get pharmaceutical drugs transported across the skin and into the body. Thus, for example, in passive transdermal drug delivery, a drug delivery patch is placed on the skin, and the rate at which the patient receives the drug is limited by how quickly (or slowly) the drug can diffuse across the skin. Additionally, such passive transdermal delivery systems often require frequent replacement of the transdermal patch. Further, passive transdermal systems often do not provide customizable drug delivery, making them less suitable for clinical applications that require a fast or controlled onset, such a quick delivery of nicotine to decrease cigarette cravings or a timely delivery of Parkinson's drugs to counteract Parkinson's symptoms.

Described herein are systems and methods to address limitations of existing transdermal drug delivery systems.

SUMMARY OF THE DISCLOSURE

Described herein are drug and other active agent delivery systems and devices for delivering active agents to skin or mucosa of a subject, and methods of delivering such active agents, and in particular, for controlling the timing and amount of drug and other active agent delivery.

In general, in one embodiment, a transdermal delivery system includes an active agent integrated with or fluidically connected to a transdermal membrane and a temperature control element. The transdermal membrane is configured to allow the active agent to flow therethrough to skin of a subject. The temperature control element is configured to heat and/or cool a portion of the transdermal delivery system so as to provide pulsatile delivery of the active agent through the transdermal membrane.

This and other embodiments can include one or more of the following features. The temperature control element can include an electromagnetic energy source. The temperature control element can include a resistive element. The temperature control element can include inductive coil or an electromagnet. The temperature control element can include a coolant or heat sink. The portion of the transdermal membrane can include a polymer configured to be heated or cooled to thereby change active agent flow. The portion of the transdermal membrane can include a glass transition polymer configured to be heated or cooled to thereby change active agent flow. The portion of the transdermal membrane can include a magnetic nanoparticle configured to be heated or cooled to thereby change active agent flow. The active agent can include nicotine or a nicotine agonist. The active agent can include a Parkinson's disease treatment. The active agent can include at least one of benztropine, carbidopa, dopamine, a dopamine analog, a dopamine antagonist, a dopamine agonist, entacapone, levodopa (L-dopa), pramipexole, rasagiline, ropinirole, rotigotine, safinamide, selegiline, both carbidopa and levodopa, trihexyphenidyl and tolcapone. The transdermal delivery system can further include an adhesive in the transdermal membrane configured to adhere the transdermal membrane to the subject. The transdermal delivery system can further include an adhesive in the transdermal membrane, and the adhesive can contain the active agent. The transdermal delivery system can further include a temperature sensor configured to measure the temperature of at least one of the temperature control element, the portion of the transdermal delivery system, or the transdermal membrane. The transdermal delivery system can further include a reservoir of active agent. The transdermal delivery system can further include a power source configured to provide power to the temperature control element. The transdermal delivery system can further include a circuit board. The transdermal delivery system can further include a microcontroller configured to control delivery of a stimulus from the temperature control element. The transdermal delivery system can further include a communication element configured to receive or transmit data and the communication element can include Bluetooth or WiFi.

In general, in one embodiment, a method of transdermally delivering an active agent, includes (1) actively heating or cooling a portion of a transdermal delivery system for a first amount of time; and (2) after the first amount of time, actively heating or cooling the portion of the transdermal delivery system for a second amount of time. The actively heating or cooling steps provide pulsatile delivery of active agent from a transdermal membrane of the transdermal delivery system to skin of a patient.

This and other embodiments can include one or more of the following features. The heating or cooling steps can include delivering heat to the portion of the transdermal delivery system. The actively heating or cooling steps can include removing heat from the portion of the transdermal delivery system. At least one of the actively heating or cooling steps can include delivering electromagnetic radiation to the portion of the transdermal delivery system. The method can further include repeating the actively heating or cooling steps at least once. The method can further include repeating the actively heating or cooling steps at least twice. The portion of the transdermal delivery system can be increased in temperature by at least 4° C. during the actively heating and cooling steps. The method can further include actively heating skin of the subject adjacent the transdermal membrane by at least 3° C. during the actively heating or cooling steps. At least one of the actively heating or cooling steps can be performed while the subject is sleeping.

In general, in one embodiment, a transdermal delivery system includes an active agent, a transdermal membrane, and a temperature control element. The active agent is integrated with or fluidically connected to a transdermal membrane. The transdermal membrane is configured to allow the active agent to flow therethrough to skin of a subject. The temperature control element is configured to provide a stimulus to a portion of the transdermal delivery system so as to provide pulsatile delivery of the active agent through the transdermal membrane to the skin of the subject.

This and other embodiments can include one or more of the following features. The system can further include a reactive material configured to prevent the active agent from flowing across the transdermal membrane until the stimulus is applied. The reactive material can include an epoxy, a polyethylene, a polymethacrylate, a polypropylene, a polypropylene glycol, a polyvinylacetate, a polystyrene, a polytetrafluoroethylene, a poly(bisphenol A carbonate), a poly(ethylene terephthalate), a polylactic acid (PLA), a polyglycolic acid (PGA), or a polyurethane. The reactive material can include a polymer, a hydrogel, a solvent, gold covered nanoparticles, or magnetic nanoparticles.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
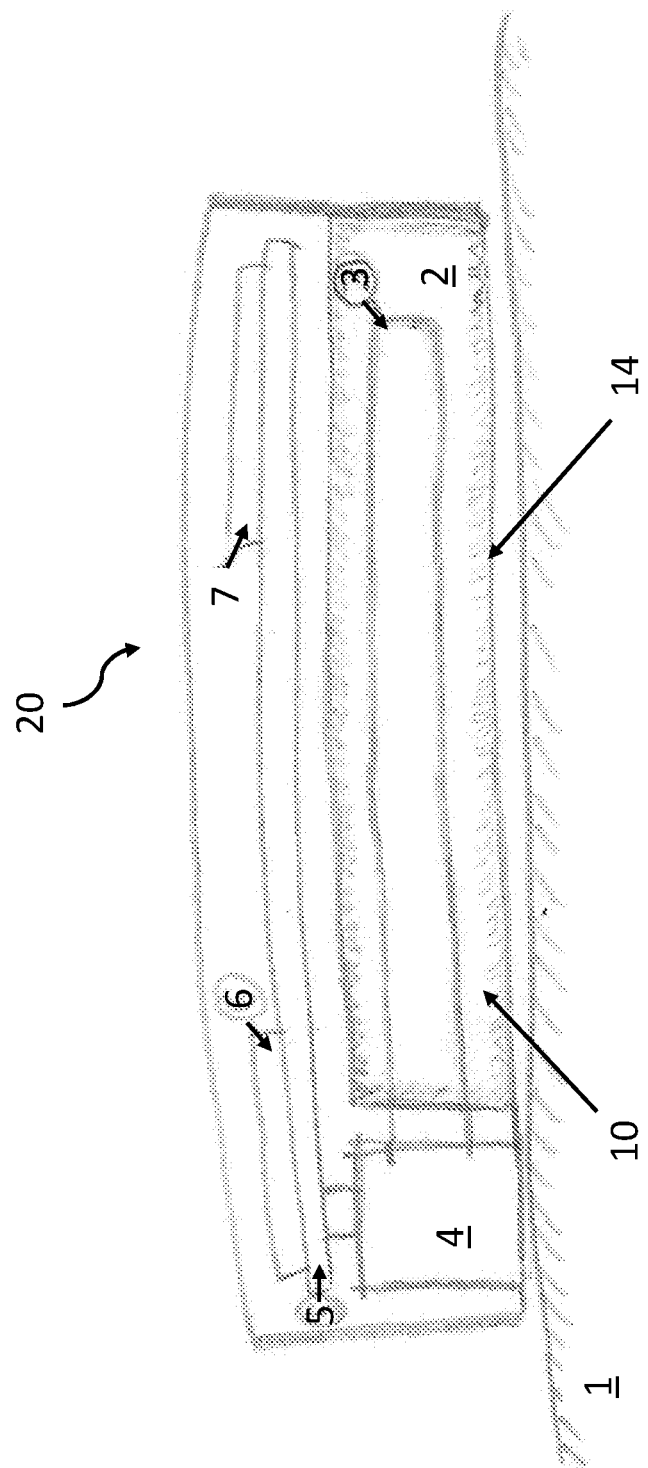
FIG. 1 shows a transdermal delivery system with temperature control for controlling active agent delivery to a subject.

Transdermal delivery systems, devices, and methods are described herein for delivering an active agent, such as a drug, to a subject. For example, described herein are transdermal delivery systems configured to control delivery of one or more active agents to a skin or mucosal surface of a subject and methods of using such systems. The active agent may be any agent useful for furnishing pharmacological activity or other effect in the diagnosis, cure, mitigation, treatment, or prevention of a disorder, a disease, a symptom, a syndrome and/or to affect any structure or any function of a human or other body. The active agent may act on the skin or mucosal surface and/or move into the blood stream, where it may travel systemically.

In some embodiments, the transdermal delivery systems described herein can be used to provide an active agent at a steady state level in the bloodstream. For example, the transdermal delivery systems can be used to provide an extended release medicine to provide a steady state of relief to manage chronic pain. In other embodiments, the transdermal drug delivery systems described herein can be used to provide an active agent such that the level of active agent varies in the bloodstream change over time. For example, the transdermal delivery systems can be used to deliver nicotine at particular times for smoking cessation. A habitual smoker who is trying to give up smoking can have very powerful cravings for cigarettes at particular times, such as upon waking up after a night's sleep and after eating a meal. Since a dose of nicotine can help manage intense cravings, it may be advantageous to give such a person a dose of nicotine only at certain times, e.g., when the cravings are strongest.

In general, the transdermal delivery systems described herein include an active agent integrated with or fluidically connected to a transdermal membrane, a transdermal membrane configured to allow active agent to flow therethrough, and a temperature control element configured to stimulate a portion of the transdermal delivery system (e.g., a transdermal membrane or an active agent therein) so as to control the timing and/or amount of delivery of the active agent through the transdermal membrane. In some embodiments, the temperature control element is a heating and cooling element configured to heat and/or cool a portion of the transdermal delivery membrane so as to provide pulsatile delivery of the active agent through the transdermal membrane. The transdermal systems described herein can be configured to control an amount and a timing of active agent delivery through the transdermal delivery system.

The transdermal systems described herein can be configured to release an active agent through the transdermal membrane to a subject in a pulsatile flow. As a result, the flux (the amount of active agent that crosses the skin per unit area per unit time) can be controlled and tuned up and down. For example, the flux can be controlled so as to deliver active agent for 1 delivery cycle (with 1 peak and 1 valley), 2 delivery cycles, 3 delivery cycles, or more than 3 delivery cycles. Each delivery cycle may be from a few minutes to many hours or even a day or more. Further, different delivery cycles may advantageously last for different lengths of time.

When fluid is delivered during a delivery cycle, it may be referred to a pulse of active agent delivery. The transdermal delivery systems described herein can control the period of time over which a desired amount of an active agent flows across a transdermal membrane for any given cycle.

In any of the delivery systems described herein, the concentration of active agent in the transdermal membrane available for delivery to a subject may be alternately increased and decreased, allowing for alternately increased and decreased flow (including down to no flow) of active agent across the transdermal membrane to the subject. In some embodiments, the transdermal systems described herein may be able to alternately heat and cool a portion of the transdermal delivery system to increase and decrease the concentration of active agent in the transdermal membrane.

The drug delivery systems and methods described herein can heat, cool, or otherwise stimulate the skin to control the flux of active agent therethrough. That is, once flow of active agent has reached skin of a subject, flow of the active agent across the skin of the subject is modulated by characteristics of the skin, such as skin composition and skin temperature. In some embodiments, a portion of the subject's skin, such as skin adjacent to the transdermal membrane, may be stimulated, such as by heating and cooling, to modulate active agent delivery across the skin.

FIG. 1 shows a transdermal delivery system 20 with temperature control element 3, power source 4, and transdermal membrane 10. Active agent 2 is integrated with transdermal membrane 10. Adhesive matrix 14 adheres transdermal delivery system 20 to skin 1 of the subject. Transdermal membrane 10 is configured to allow the active agent 2 in the transdermal membrane 10 to flow therethrough to skin 1 of the subject. Power source 4 is configured to provide power to the temperature control element 3 and may be a rechargeable or non-rechargeable battery such as a lithium metal, lithium ion, nickel metal hydride, or nickel cadmium battery. If rechargeable, power source 4 may be rechargeable using a wired or wireless mechanism, such as using wireless inductive recharging from a smart phone.

Temperature control element 3 can be positioned at least partially within transdermal membrane 10. The temperature control element 3 may include one or more resistive heating elements, infrared light sources, or chemicals for exothermic chemical reactions. In some embodiments, temperature control element 3 is configured to generate heat (e.g., kinetic energy) or other energy. Further, temperature control element 3 can deliver heat, coolant, or other energy to the transdermal membrane 10 and thereby control (increase, decrease or maintain) a temperature of the transdermal membrane 10 and/or active agent 2. The temperature control element 3 may increase temperature of a portion of the transdermal membrane 10 (and/or the active agent 2) by at least 1° C., at least 2° C., at least 3° C., at least 4° C., at least 5° C., at least 6° C., at least 7° C., at least 8° C., at least 9° C. or at least 10° C. or by not more than 1° C., not more than 2° C., not more than 3° C., not more than 4° C., not more than 5° C., not more than 6° C., not more than 7° C., not more than 8° C., not more than 9° C., or not more than 10° C., or any value between these numbers (such as at by at least 2° C. and not more than 5° C.) by the applied heat or other energy. Further, the applied heat or other energy from the temperature control element 3 can act on the transdermal membrane 10 (and/or a component in the transdermal membrane 10, such as the active agent 2) to allow or increase active agent delivery through transdermal membrane 10 to skin 1. For example, the applied heat or other energy can increase active agent diffusion and movement within transdermal membrane 10 and/or can increase the pore size of the transdermal membrane 10 to enhance flow therethrough.

In some embodiments, energy delivery to a portion of the transdermal delivery system 20, such as to the transdermal membrane 10, may alternate between two (or more) conditions, such as an "on" condition and an "off" condition. For example, a first delivery condition may have higher level of heat delivery (e.g., a delivery at a higher temperature and/or delivery for a longer time), and a second delivery condition may have a lower level (including no) heat delivery (e.g., lower temperature and/or for a longer time). A higher level of heat delivery can be sufficiently high so as to enable flow of a sufficient amount of active agent across the transdermal membrane 10 to skin 1 to have a therapeutic, prophylactic, or other effect. In contrast, a lower heat delivery state can be sufficiently low (or be off) such that there is insufficient (or no) flow of active agent across transdermal membrane 10 and therefore no therapeutic or prophylactic effect. In some embodiments, the transdermal delivery system 20 may alternate repeatedly between higher and lower heat delivery conditions to create pulsatile active agent delivery (e.g., a plurality of pulses of active agent delivery). For example, the transdermal delivery system 20 may produce 1 pulse, 2 pulses, 3 pulses, 4 pulses, 5 pulses, 6 pulses, 7 pulses, 8 pulses, 9 pulses, or 10 pulses or more than 10 pulses.

In some embodiments, a lower (or no) heat delivery state may result from temperature control element 3 being off or inactive, thereby reducing or eliminating heat delivery to a portion of the transdermal delivery system 20. In some embodiments, temperature control element 3 may be configured (e.g., may have a refrigerant or act as a heat sink) to actively decrease a temperature of a portion of the transdermal delivery system 20. The lower (or no heat) delivery or active cooling by the temperature control element 3 may reduce the temperature of a portion of transdermal delivery system 20 (elative to the temperature of that portion of the transdermal delivery system 20 or relative to the temperature of that portion of the transdermal delivery system 20 that has previously been heated) by at least 1° C., at least 2° C., at least 3° C., at least 4° C., at least 5° C., at least 6° C., at least 7° C., at least 8° C., at least 9° C., or at least 10° C. or by not more than 1° C., not more than 2° C., not more than 3° C., not more than 4° C., not more than 5° C., not more than 6° C., not more than 7° C., not more than 8° C., not more than 9° C., or not more than 10° C. or any value between these numbers (such as by at least 2° C. and not more than 5° C.). In some embodiments, the temperature of a portion of the transdermal delivery system 20 in place on the user's skin may be about 30° C. (e.g., between 29.5° C. and 30.5° C.), about 31° C., about 32° C., about 33° C., about 34° C., about 35° C., about 36° C., about 37° C., about 38° C., or about 39° C. (e.g., +/−0.5° C.). As the temperature of the user's skin may be cooler than the user's body or blood temperature (e.g., about 32° C., about 33° C., or about 34° C. rather than about 36° C. or about 37° C.), the baseline temperature of part of the transdermal delivery system 20 in place on the user may be about 32° C., about 33° C., or about 34° C., and the transdermal delivery system 20 may be configured to not deliver active agent at such temperatures.

In some embodiments, the transdermal delivery system 20 may be configured to heat or cool the user's skin instead of, or in addition to, heating or cooling a portion of the transdermal delivery system 20. Such heating or cooling may alter active agent delivery through the skin, such as allowing or reducing active agent delivery. Thus, the temperature control element 3 may be configured to deliver heating or cooling or other energy to skin 1 of the subject to heat or cool the skin 1. The temperature control element 3 may deliver heating or cooling or other energy to skin 1 indirectly (e.g., through conduction, such as a heated or cooled transdermal membrane) directly or (e.g., via infrared energy delivery to heat the skin). Heating of the skin may allow the flux (amount of active agent that crosses the skin per unit area per unit time) to exceed that which is typically observed in transdermal delivery (e.g., in passive transdermal delivery systems) and/or that which is achieved without heating. This increased flux may be useful, for example, for getting active agents that are not readily deliverable by other transdermal systems delivered across the skin or for controlling pulses of active agent delivery. In some embodiments, both the transdermal membrane 10 and the skin 1 can be heated in response to the applied heat or other energy.

In some embodiments, the upper limit, lower limit, or range of desired temperatures for the portion of transdermal delivery system 20 to be heated or cooled (and/or the temperature of the skin) may be tuned to the particular system for desired efficacy, comfort, and safety. That is, too high of a temperature may be uncomfortable or may burn a subject. Too low of a temperature may not facilitate sufficient delivery of a desired amount of active agent. For example, a system 20 configured for delivering a larger amount of an active agent through the front of the arm (dorsal arm skin) may have a higher maximum temperature than a system 20 for delivering a smaller amount of an active agent through the neck. The temperature of skin 1 may be heated so that it is at least 32° C., at least 33° C., at least 34° C., at least 35° C., at least 36° C., at least 37° C., at least 38° C., at least 39° C., or at least 40° C. or to a temperature not more than 40° C., 39° C., 38° C., 37° C., 36° C., 35° C., or 34° C. or any temperature in between these numbers. The temperature of skin 1 may be increased by at least 1° C., at least 2° C., at least 3° C., at least 4° C., at least 5° C., at least 6° C., at least 7° C., at least 8° C. or by not more than 1° C., not more than 2° C., not more than 3° C., not more than 4° C., not more than 5° C., not more than 6° C., or not more than 7° C., or any value between these numbers (such as at by least 2° C. and by not more than 5° C.) by the applied heat or other energy.

The transdermal delivery system 20 may be configured to provide pulsatile delivery of active agent. Pulsatile delivery includes an "on" period of active agent delivery and an "off" period without or with a low level of active agent delivery. Temperature control element 3 may alternate between a period of heating and a period of non-heating (or cooling). Alternating a period of heating for delivering active agent with a period of non-heating (or cooling) may lead to active agent delivery with 1 pulse, 2 pulses, 3 pulses, 4 pulses, or 5 or more than 5 pulses of active agent delivery for pulsatile delivery of the active agent 2. A delivery window during which a therapeutically effective or otherwise desired dosage of an active agent is delivered from the transdermal delivery system 20 may last at least 10 minutes, at least 30 minutes, at least 1 hour, at least 2 hours, at least 3 hours, at least 4 hours, at least 6 hours, at least 8 hours, at least 10 hours, at least 12 hours, or at least 18 hours, or less than 10 minutes, less than 30 minutes, less than 1 hour, less than 1 hour, less than 2 hours, less than 3 hours, less than 4 hours, less than 6 hours, less than 8 hours, less than 10 hours, less than 12 hours, or less than 18 hours. An "off" period during which active agent delivery is "off" (or an ineffective or untherapeutic amount of active agent is delivered) may last at least 10 minutes, at least 30 minutes, at least 1 hour, at least 2 hours, at least 3 hours, at least 4 hours, at least 5 hours, at least 6 hours, at least 10 hours, at least 12 hours, at least 18 hours, at least 1 day or less than 10 minutes, less than 30 minutes, less than 1 hour, less than 2 hours, less than 3 hours, less than 4 hours, or less than 6 hours, less than 10 hours, less than 12 hours, less than 18 hours or less than 1 day or anything in between these amounts. In some embodiments, active agent delivery is "off" most of the time when a subject is planning on sleeping and then is on before the subject plans to wake up, such as one hour before the subject plans to wake up. Active agent delivery may be "on" for several pulses based on a subject's planned activities such as before the subject plans to wake up (e.g., starting one hour before), at a planned lunch time (e.g., starting 30 minutes before) and at a planned dinner time (e.g., starting 30 minutes before). The amount of active agent delivery during "on" periods may be substantially the same for each period or may be different for the different periods. For example, greater amounts of active agent may be delivered during the wake up period than at the lunch period.

FIG. 1 also shows flexible circuit board 5 and microcontroller 6 in transdermal delivery system 20 useful for controlling the active agent delivery system. Microcontroller 6 may include a processor, memory, and input/output peripheral for controlling transdermal "on" and "off" parameters. Microcontroller 6 be preprogrammed to control temperature control element 3 for turning heat or other energy on and off. Microcontroller 6 may control time of heating/no (or little) heating for temperature control element 3 as well as the number of pulses of heat/no (or little) heat. Microcontroller 6 may also control the temperature of heating/no (or little) heating. The transdermal delivery system 20, such as temperature control element 3 or transdermal membrane 10, may include a temperature sensor, such as a thermometer for measuring temperature. The temperature sensor may provide feedback to the system to stop (or reduce) heating or to start heating once a portion of the system reaches a particular temperature. The limit may be useful for limiting an amount of active agent delivery (e.g., to prevent an overdose or more active agent than desired) or to prevent discomfort or prevent a burn to the subject.

FIG. 1 also shows communication module 7 in transdermal delivery system 20. Communication module 7 may be configured to connect and communicate with an external data source, such as a smart phone, a tablet, a computer, a server, or the internet (a TCP/IP network). Communication may be by wire or may be wireless such as using Bluetooth, Bluetooth Low Energy, WiFi, WiMAX, or Zigbee technology. Communication module 7 may send data from the transdermal delivery system 20 to the external source, such as data about transdermal membrane usage, one or more temperatures of one or more portions of transdermal delivery system 20, or duration of particular temperatures in one or more portions of the transdermal delivery system 20. Communication module 7 may receive data from a user, such as data for controlling: active agent delivery time and duration, temperature changes and duration of heating, and/or number of active agent delivery pulses. In some embodiments, the user may send signals to communication module 7 from a smart phone.

The transdermal membrane 10 may be adhered or configured to adhere to the skin 1 or mucosal surface of a subject, such as through a removable adhesive matrix 14. In some embodiments, the adhesive matrix 14 may be sufficiently strong such that it is able to hold the transdermal delivery system 20 in place on skin 1 with or without a band or other fastener. The adhesive matrix 14 may include an acrylate, a methacrylate, or an epoxy diacrylate for adhering. The adhesive matrix 14 may be configured to substantially seal the transdermal membrane 10 of the system to the subject's skin or mucosa. The adhesive matrix 14 may be configured to minimize or prevent significant entry of air or contaminants from the environment to the transdermal membrane 10. In one embodiments, the adhesive matrix 14 may be configured to prevent a solvent (e.g., in the transdermal membrane) from unwanted evaporation during transdermal system use. In some embodiments, the adhesive matrix 14 contains the active agent 2. For example, active agent 2 may be dispersed or dissolved in part or all of the adhesive matrix 14. The adhesive matrix 14 may hold part(s) of the transdermal system 20 together, and/or contain the active agent 2 and/or hold the transdermal system 20 to the subject.

FIG. 1 also shows flexible circuit board 5 and microcontroller 6 for controlling the active agent delivery system. Microcontroller 6 may be preprogrammed to control periods of heating/no heating of a portion of the transdermal delivery system 20. Microcontroller 6 may also or instead be programmed to control periods of heating/no heating from received instructions, such as from a user interface on the transdermal delivery system 20 or from an external communication, such as instructions delivered using communication module 7.

By controlling periods and levels of heating/no heating (cooling), a pulsatile delivery can be achieved from the transdermal membrane 10. The control mechanisms described herein allow the delivery of the active agent 2 to be controlled to meet the clinical need for variable active agent delivery, such as increasing therapeutic or other effect when a symptom being targeted is problematic and not at times when the symptom is not as problematic. For example, smokers often experience a craving for a cigarette at particular times, such as intense cravings when first awaking after sleep. A controlled dose of nicotine given to a subject at the right time may control such a craving and keep a person from smoking upon waking. Using the transdermal delivery system 20 with heating and cooling as described herein, for example, allows a smoker to receive a nicotine dose when their cravings are normally particularly troublesome. A dose of active agent 2 may be given when needed or in anticipation of a need. A dose of the active agent 2 may be given to a subject when a subject is awake or when they are asleep. For example, some symptoms or health issues (e.g., cigarette cravings, heart attacks, or migraine headaches) can be especially troublesome in the morning or upon awakening. Using the transdermal delivery systems described herein, a dose of the active agent 2 can be started before the subject plans to wake up, such as at least 15 minutes, at least 30 minutes, at least 45 minutes, at least 1 hour, at least 2 hours, or at least 3 hours before the subject plans to wake up.

Additionally, by tuning the properties of the transdermal system 20 so that delivery of the active agent 2 is lessened or essentially non-existent in the absence of applied heat, no or subclinical levels of active agent dosages can be delivered, effectively turning off the active agent effects in those periods. This may be achieved with an active agent/excipient/matrix adhesive such that diffusion of the active agent is minimal at unheated temperatures (e.g., 32° C. or skin temperature), but diffusion can be increased significantly when heated. For example, by incorporating excipients and/or adhesives with melting or glass transition temperatures above skin temperature (e.g., 32° C.) into the transdermal membrane 10, the membrane 10 matrix can allow diffusion of the drug from the transdermal membrane 10 to the skin upon heating. In one embodiment, small molecules or polymeric components with appropriate melting point or glass transition temperatures can be incorporated into the transdermal membrane 10. This is in contrast to common transdermal matrix systems, which typically deliver active agent as soon as applied to the subject according to their active agent concentration driven controlled-release kinetics.

Figure 2:
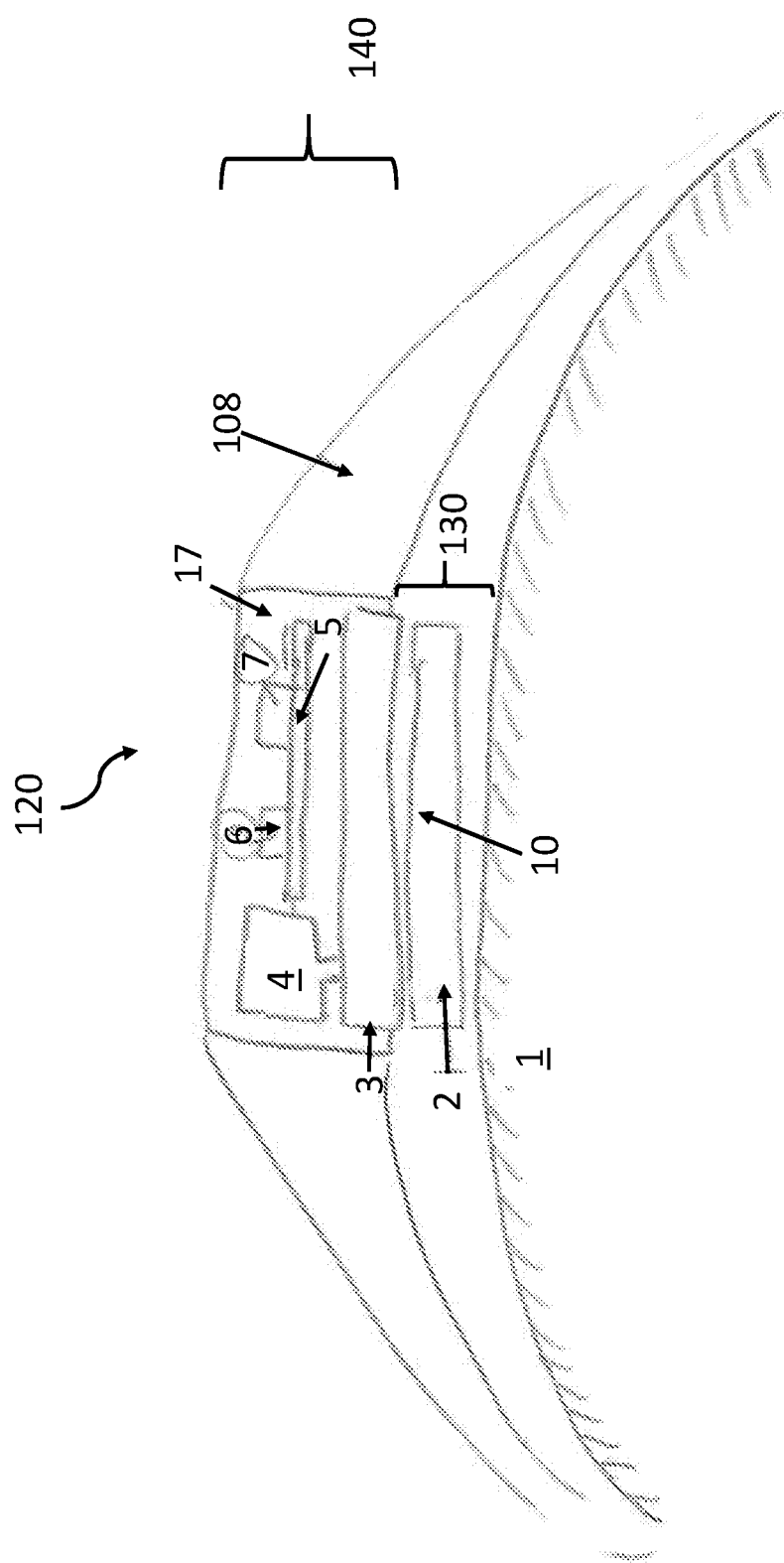
FIG. 2 shows another transdermal active agent delivery system with temperature control for controlling active agent delivery to a subject.

FIG. 2 shows another transdermal delivery system 120 with temperature control element 3 and transdermal membrane 10 containing active agent 2 for delivery to a subject. Transdermal delivery system 120 is similar to transdermal delivery system 20, but has two interconnectable parts 130, 140 and a band 108. The first part 130 includes transdermal membrane 10. The second part 140 includes the band 108 and housing 17 (which includes temperature control element 3, power source 4, flexible circuit board 5, microcontroller 6, and communication chip 7). The temperature control element 3 is configured to actively heat and/or actively cool a portion of the transdermal delivery device (e.g., transdermal membrane 10) as described herein. In some embodiments, the first part 130 can be disposable and the second part 140 can reusable.

As shown in FIG. 2, the band 108 can be connected to housing 17 and is configured to hold housing 17 close to a subject. Band 108 may be configured to wrap around a subject's body, such as an arm or leg to hold housing 17 close to the subject. In some embodiments, band 108 may hold both first part 130 and second part 140 against a subject's body. First part 130 may additionally include an adhesive (as described above) with respect to FIG. 1, which may hold transdermal membrane 10 against a subject's body. In some embodiments, first part 130 is separable from second part 140. For example, first part 130 and second part 140 may connect, such as through mating magnets on each part or mating snap-fit parts. In some other embodiments, first part 130 and second part 140 may be integral, e.g., not separable. In some embodiments, housing 17 may not contain all of the elements of the temperature control element 3, power source 4, flexible circuit board 5, microcontroller 6, and communication chip 7. For example, housing 17 may contain temperature control element 3 while communication chip 7 may be absent or may be contained in first part 130.

Figure 3:
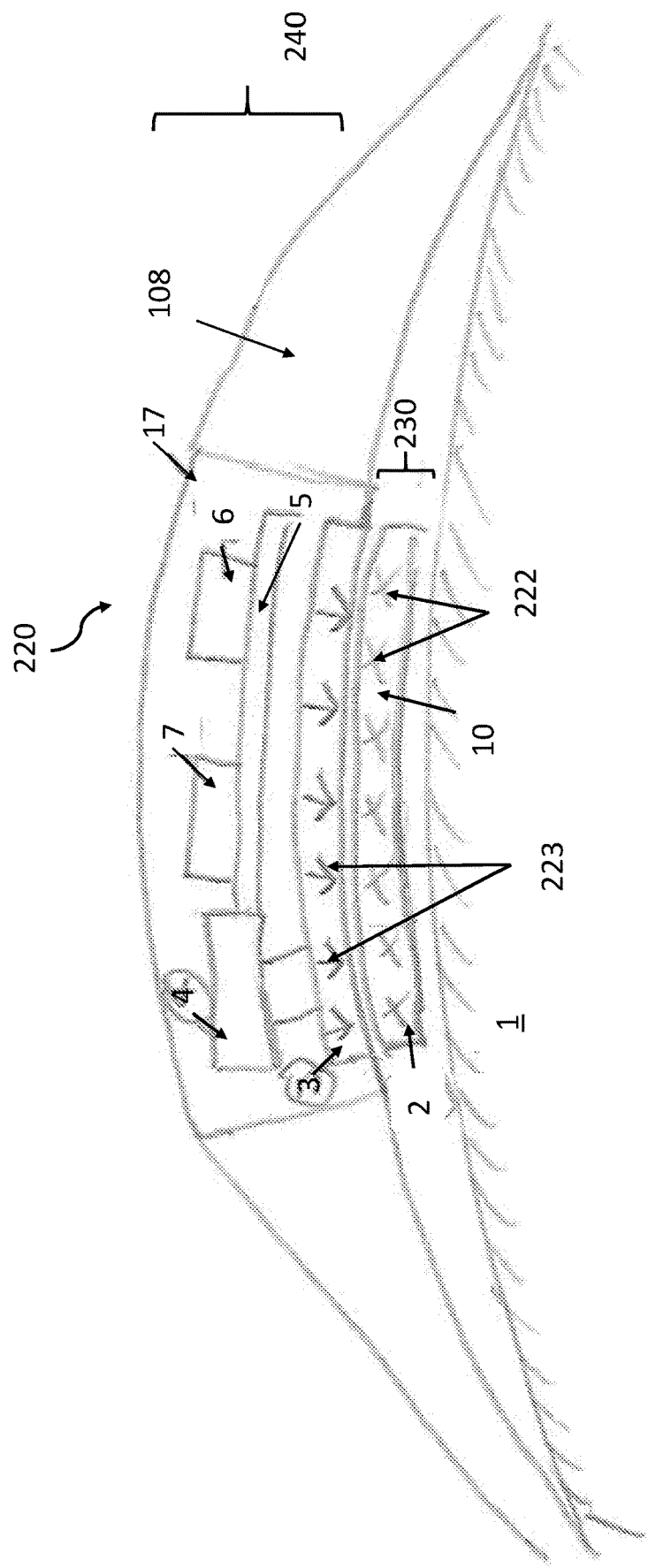
FIG. 3 shows a transdermal delivery system with temperature control and a complementary transdermal membrane for controlling active agent delivery to a subject.

FIG. 3 shows another transdermal delivery system 220 useful for controlling active agent delivery to a subject. Delivery system 220 is similar to system 120 (and includes two parts 230, 240) except that the first part 230, which can be disposable, contains reactive material 222 to hold or otherwise prevent the active agent 2 from flowing across the transdermal membrane, and the second part 240, which can be reusable, is configured to produce stimulus 223 to act on the reactive material 222 and control the active agent 2 flow. The delivery system 220 thus includes the transdermal membrane 10 with reactive material 222 and active agent 2 and temperature control element 3 configured to provide a stimulus 223 to reactive material 222 to control active agent 2 flow. The reactive material 222 can be a plurality of small molecules, a solvent, or a polymeric material that is responsive to the stimulus 223 from the temperature control element 3. The reactive material 222 may include, for example, a polymer with a desired glass transition profile, a solvent, gold covered nanoparticles responsive to heat, and/or magnetic (e.g., iron) nanoparticles responsive to electromagnetic radiation. For example, reactive material 222 may be a polymer having a glass transition temperature ($T_g$) configured to transition from a first form to a second form at a desired temperature. In the first form, the polymer may have a hard, solid, and/or glassy state that prevents or minimizes active agent 2 flow and in the second form, the polymer may have a softer, more rubbery, and/or more viscous state that allows active agent flow. The stimulus 223 may be heat or other energy from the temperature control element 3 configured to transition the polymer from the first form to the second form. The reactive material 222 may be in a relatively hard, solid and/or glassy state at lower temperatures, such as at room temperature and/or skin temperature (e.g., at less than 32° C., less than 33° C., less than 34° C., or less than 35° C.). The reactive material 222 may be in a softer, more rubbery, and/or more viscous state at higher temperatures, such as above room temperature and skin temperature, (e.g., at least 34° C., at least 35° C., at least 36° C., at least 37° C., at least 38° C., at least 39° C., or at least 40° C.). The reactive material 222 may prevent substantial diffusion of the active agent 2 when the reactive material 222 is in the relatively hard, solid and/or glassy state at a lower temperature. The reactive material 222 may release or otherwise allow the active agent 2 to flow to the skin 1 of a subject when the reactive material 222 is in the softer, more rubbery, and/or more viscous state at a higher temperature. For example, the reactive material 222 may include an epoxy, a polyethylene, a polymethacrylate, a polypropylene, a polypropylene glycol, a polyvinylacetate, a polystyrene, a polytetrafluoroethylene, a poly(bisphenol A carbonate), a poly(ethylene terephthalate), a polylactic acid (PLA), a polyglycolic acid (PGA), and/or a polyurethane. The reactive material 222 may be tuned to have a desired glass transition temperature useful for holding and releasing a particular active agent in the transdermal system such as by including or excluding bulky, inflexible side groups, having relatively shorter or longer side chains, having a greater or lesser degree of crosslinking, or including or excluding a plasticizer such as nitrobenzene, B-napthyl salicylate, carbon disulphide, glycerine, propylene glycol, triethyl citrate, triacetine, polyethylene glycol, having greater or less hydrophobicity. In some examples, the reactive material 222 may include a polymeric hydrogel.

As indicated above, the delivery system 220 can include temperature control element 3 configured to deliver the stimulus 223 to reactive material 222 to control flow of active agent 2. The stimulus 223 from temperature control element 3 may be, for example, kinetic energy, a magnetic force, an electrical pulse, infrared radiation, or electromagnetic radiation. Temperature control element 3 may include chemicals (e.g., calcium chloride, iron particles, supersaturated sodium acetate), an electromagnet, an inductive coil, an infrared light source, phase change materials, and/or a visible light source to provide the stimulus 223.

In some variations, the stimulus 223 may be configured to act on the reactive material 222 such that the reactive material 222 holds or otherwise prevents active agent 2 from flowing across the transdermal membrane 10 to a subject. Turning the stimulus 223 off can allow a pulse of active agent 2 to flow across the transdermal membrane 10 to a subject. The cycle may be repeated multiple times to provide pulsatile active agent delivery, as described elsewhere herein.

In some embodiments, the transdermal system 220 may include two or more different types of reactive materials, and the transdermal system 220 may be configured to control pulsatile delivery of the active agent 2 or to control delivery of two different kinds of active agent 2. For example, a first type of reactive material 222 may have a first glass transition temperature (Tg) and may release its payload of active agent 2 at a first (lower) temperature (e.g., 36° C.) while a second type of reactive material 222 may have a second glass transition temperature (Tg) component and may release its payload of active agent 2 at a second (higher) temperature (e.g., 39° C.). Active agent delivery may be controlled by first delivering a first stimulus 223 to a portion of the transdermal system so the first type of reactive material 222 releases its payload of active agent 2, optionally turning the first stimulus 223 off, and delivering a second stimulus 223 to a portion of the transdermal system so the second type of reactive material 222 releases its payload of active agent 2. Such first and second payloads may release the same kind of active agent 2 (e.g., in a pulsatile manner) or may release different types of active agents.

Although the reactive material 222 may be in the transdermal membrane 10, it can additionally or alternatively be in another part of the transdermal delivery system 220 and may be configured to control pulsatile delivery. For example, the reactive material 222 can be in an active agent reservoir. The active agent reservoir can be separate from the transdermal membrane 10 and may be fluidically connected to it. The active agent reservoir may be configured to hold active agent 2. The stimulus 223 can act on the reactive material 222 in the active agent reservoir to release the active agent 2 from the active agent reservoir and into the transdermal patch. The stimulus 223 can allow release of active agent 2 from the active agent reservoir all at one time. Alternatively, the stimulus 223 can allow pulsatile release of active agent 2 from the active agent reservoir. An active agent reservoir may be in any of the delivery systems described herein, and may be in a first part or a second part of the delivery system.

In some variations, the active agent 2 can be the reactive material 222 responsive to stimulus 223, and there is can be no separate reactive material 222 that controls active agent flow through the transdermal membrane 10. In some embodiments, stopping stimulus 223 stops or significantly slows releasing, heating or another mechanism otherwise allowing active agent to flow across transdermal membrane 10. Significantly slowing the releasing, heating or other mechanism allowing active agent flow reduces the level of active agent flow relative to the "on" or stimulated level, such that even if some active agent is flowed across the transdermal membrane 10, it does not have the "on" effect and may be sufficiently low to have no therapeutic or detectable effect on the subject. In some embodiments, a stimulus 223 from temperature control element 3 may act on reactive material 222 to actively stop reactive material 222 from releasing or flowing active agent across transdermal membrane 10. For example, temperature control element 3 may include a heat sink, an endothermic ventilation fan, an evaporative based cooling mechanism, a sublimation based cooling mechanism, cyclic refrigeration, thermoelectric refrigeration, or magnetic refrigeration and may be configured to cool reactive material 222 and prevent active agent flow to a subject. In some embodiments, the temperature control element 3 may be configured to deliver both an "on" stimulus such as heat to turn on active agent flow across the transdermal membrane 10 and an "off" stimulus such as refrigeration to prevent or decrease active agent flow across the transdermal membrane 10.

Any of the transdermal systems described herein may have a discreet or low profile. Such a system may be worn with minimal notice by the user (or others) or with no or minimal discomfort while sleeping. In some embodiments, the transdermal system may be less than 50 $cm^3$ in volume, less than 25 $cm^3$ in volume, (e.g., 5 cm×10 cm×0.5 cm), less than 20 $cm^3$ in volume, less than 15 $cm^3$ in volume or less than 10 $cm^3$ in volume. In some embodiments, the transdermal system may have dimensions that are less than 5 cm on a first side, less than 10 cm on a second side, and less than 0.5 cm on a third side. In some embodiments, the transdermal system may weigh less than 60 grams, less than 30 grams, less than 20 grams, less than 10 grams or less than 5 grams.

Any of the transdermal systems described herein may be very quiet (or silent) during use such as producing less than 20 dB, less than 10 dB, or less than 5 dB of sound during use.

In some embodiments, the transdermal systems may be held to a subject, such as by using the band 108 or strap that wraps around part of a user's body. The adhesive may be configured to adhere the transdermal system against the user's skin only using the adhesive. In some embodiments, the system may be sufficiently small, lightweight or flat such that the adhesive can readily hold the system in place on a user without the use of the band 108 or strap. The transdermal systems may be configured to be placed in any desired location on a user's body (e.g., abdomen, arm, back, leg, scalp, upper arm) using adhesive 14 and/or band 108.

Also described herein are methods for transdermally delivering an active agent. Some methods include actively heating or cooling a portion of a transdermal active agent delivery device for a first amount of time. Some methods include the step of after the first amount of time, actively heating or cooling the portion of the transdermal active agent delivery device for a second amount of time. In some such methods, the actively heating or cooling steps provide pulsatile delivery of active agent from a transdermal membrane of the transdermal active agent delivery device to skin of a patient. In some methods, the actively heating or cooling steps comprises delivering pulsatile heat to the portion of the drug delivery device. In some methods, the actively heating or cooling steps comprises removing heat from the portion of the transdermal active agent delivery device. In some methods, at least one of the actively heating or cooling steps comprises delivering electromagnetic radiation to the portion of the drug delivery device. Some methods include repeating the actively heating or cooling steps at least once. Some methods include repeating the actively heating or cooling steps at least two times. Some methods include repeating the actively heating or cooling steps at least three times. In some methods, the portion of the transdermal delivery system is heated by at least 4° C. Some methods include actively heating skin of the subject adjacent the transdermal membrane by at least 3° C. In some methods, at least one of the actively heating or cooling steps is performed while the subject is sleeping.

Figure 4:
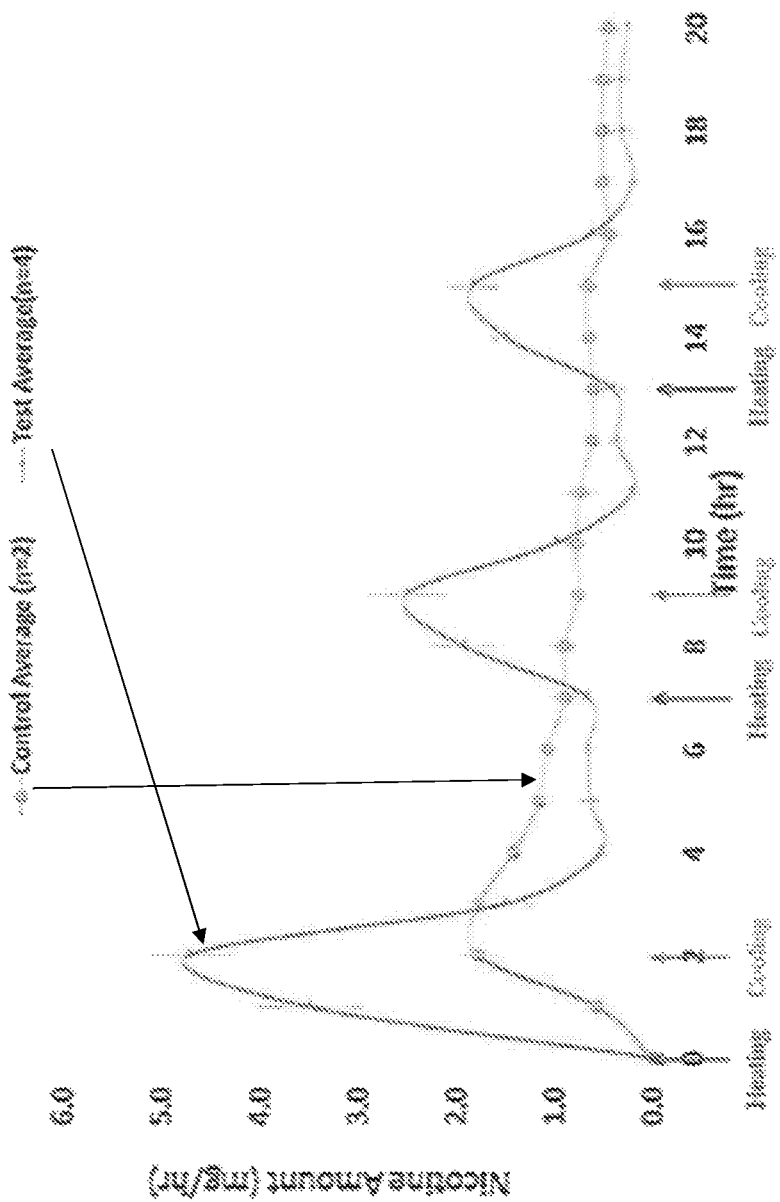
FIG. 4 shows results of nicotine delivery after heating a matrix-type transdermal membrane to deliver nicotine through the transdermal membrane.

FIG. 4 shows results from using a transdermal delivery system as described herein with periodic heating and cooling. Experiments were carried out by applying passive matrix-type nicotine patches containing 21 mg of nicotine to human cadaver skin and then periodically heating and cooling the patches over a period of 20 hours. Controls with no heating and cooling were tested concurrently. The test patches were subject to 3 cycles of heating and cooling while the control patches were not. Patches were heated for 2 hours, cooled for 5 hours, heated for 2 hours, cooled for 4 hours, heated for 2 hours, and cooled. Nicotine delivery across the skin was measured and averaged for control patches (n=2) and test patches (n=4). Nicotine flow across the skin increased when heat was applied, and reached levels around 4.9 mg/hr, around 2.5 mg/hr, and around 1.8 mg/hr, respectively, during each of the three time periods when heat was applied. The level of nicotine delivery across the skin rapidly increased with heating and rapidly decreased with cooling as noted by the steep slope of increased nicotine flow after each heat application and steep decline of nicotine delivery after each cooling application. FIG. 4 shows that pulsatile active agent (nicotine) delivery was achieved by alternate cycles of heating and cooling.

Any of the systems or methods described herein, and in particular in a method for delivering an active agent to a subject, may include or be configured to include at least one of following or acceptable salts thereof, Acamprosate, Acetaminophen, Acetaminophen+Oxycodone, Alevicyn SG, Alfentanil, Allopurinol, Almotriptan, Alprazolam, Amitriptylinem, Amoxapine, Apomorphine, Aripiprazole, Armodafinil, Asenapinemaleate, Atomoxetine, Azelastine HCl, Baclofen, Benzbromarone, Benzydamine, Brexpiprazole, Budesonide, Bupivacaine, Buprenorphine, Buprenorphine+Nalaxone, Bupropion, Bupropion Hydro bromide, Bupropion Hydrochloride, Buspirone, Cabergoline, Capsaicin, Carbamazepine, Carbidopa+Levodopa, Carisprodol, Celecoxib, Citalopram, Clobazam, Clonazepam, Clonidine, Clopidogrel, Colchicine, Cyclobenzaprine, Dalteparin sodium, Desvenlafaxine, Dexamfetamine, Dexmethylphenidate HCl, Diazepam, Diclofenac, Diclofenac Potassium, Disulfiram, Divalproex Sodium, Dolasetron Mesilate, Doxepin, Dronabinol, Droxidopa, Duloxetine, Eletriptan, Entacapone, Escitalopram oxalate, Eslicarbazepine Acetate, Esomeprazole/naproxen, Estradiol, Estrogen, Eszopiclone, Ethosuximide, Etodolac, Ezogabine, Febuxostat, Felbamate, Fenbufen, Fentanyl, Fentanyl Citrate, Fentanyl HCl Flunisolide, Fluorouracil, Fluoxetine, Fluticasone propionate, Fluvoxamine, Formoterol, Fosphenytoin, Frovatriptan, Gabapentin, Granisetron, Guanfacine, Hydrocodone Bitartrate, Hydrocodone+Acetaminophen, hydrocortisone, Hydromorphone Hcl, Hydroxyzine, Hypericum Extract, Ibuprofen, Indometacin, Ketorolac, Lacosamide, Lamotrigine, Levetiracetam, Levomilnacipran, Levosalbutamol, Lidocaine, Lidocaine/Tetracaine, Lisdexamfetamine, Lithium Carbonate, Lorazepam, Lorcaserin Hydrochloride, Losartan, Loxapine, Meclizine, Meloxicam, Metaxalone, Methylphenidate, Methylphenidate Hydrochloride, Milnacipran, Mirtazapine, Modafinil, Morphine, Nabilone, Nadolol, Naltrexone, Naproxen, Naratriptan, Nedocromil, Nefazodone, Nicotine, Nicotine Sulfate, Nicotine salts, Nitroglycerin, Olanzapine, Ondansetron, Orlistat, Oxaprozin, Oxcarbazepine, Oxybutynin, Oxycodone, Oxycodone+Acetaminophen, Oxycodone Hydrochloride, Oxymorphone, Palonosetro, Pamidronate, Paroxetine, Paroxetine Mesylate, Perampanel, Phentermine+Topiramate, Phentermine Hydrochloride, Phentolamine Mesylate, Pramipexole, Prasugrel, Prazepam, Prednisone, Pregabalin, Promethazine, Propofol, Quetiapine, Quetiapine Fumarate, Ramelteon, Rasagiline, Rasagiline Mesylate, Remifentanil, Risperidone, Rivastigmine, Rivastigmine Tartrate, Rizatriptan, Ropinirole, Ropivacaine, Rotigotine, Rufinamide, Salbutamol, Scopolamine, Selegiline, Sertraline, Sodium Oxybate, Strontium, Sufentanil, Sumatriptan, Sumatriptan Succinate, Suvorexant, Tapentadol, Tasimelteon, Temazepam, Testosterone, Tetracaine+Lidocaine, Theophylline, Tiagabine, Tiotropium, TirofibanHCl, Tolcapone, Topiramate, Tramadol, Tramadol+Acetaminophen, Trazodone, Triazolam, Trimipramine Maleate, Valproate Semi sodium, Valproate Sodium, Venlafaxine, Vigabatrin, Vilazodone, Vortioxetine, Zaleplon, Zileuton, Ziprasidone, Zolmitriptan, Zolpidem, Zolpidem Tartrate, Norethisterone Acetate (NETA), Enapril, Ethinyl Estradiol, Insulin, Memantine, Methamphetamine, Norelgestromine, Pergolide, Ramipril, Tecrine, Timolol, Tolterodine and Zonisamide.

In some particular examples, the systems or methods described herein may be configured to aid in smoking cessation or to treat aspects of Parkinson's Disease. For example, in some particular examples, the systems or methods described herein may include nicotine, a nicotine analog, a nicotine antagonist, a nicotine agonist, benztropine (Cogentin), carbidopa, dopamine, a dopamine analog, a dopamine antagonist, a dopamine agonist, entacapone, levodopa (L-dopa), pramipexole (Mirapex), rasagiline (Azilect®), ropinirole (Requip), rotigotine (Neupro®), safinamide (Xadago), selegiline (Eldepryl®, Zelapar™), sinemet (both carbidopa and levodopa), and trihexyphenidyl (Artane®), and tolcapone (Tasmar).

The active agent 2 may be in the form of a solution, a suspension, a gel, or a dispersion. In some embodiments, the transdermal delivery system contains the active agent 2. In some embodiments, a transdermal delivery system as described herein may be replenished with active agent from an outside source and in some embodiments, a transdermal delivery system as described herein may not contain an active agent and may be configured to receive added active agent. For example, an active agent may be added to the transdermal delivery system by injection of active agent into the transdermal delivery system (e.g., into the transdermal membrane) or by adding an active agent reservoir configured to flow active agent to the delivery system.

It should be understood that features described with respect to one embodiment may be substituted for or used in addition to features described with respect to another embodiment.

The systems and methods described herein can further include any of the elements or steps described in U.S. Pat. Nos. 8,673,346, 9,555,277, 8,372,040, 10,105,487, 10,213,586, U.S. Publication No. 2018/0374381, PCT Publication No. WO2018/106723, PCT Publication No. WO2018/129304, PCT Publication No. WO2018/148746, PCT Publication No. WO2018/129363, U.S. Publication No. US2018/0110768, or U.S. Publication No. 2019/0054078, the entireties of which are incorporated by reference herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A transdermal delivery system comprising:
   a transdermal membrane;
   a first active agent contained within a reservoir separate from and fluidically connected to the transdermal membrane, the transdermal membrane configured to control, in response to temperature, a flow of the first active agent from the reservoir to skin of a subject; and
   a temperature control element configured to cyclically heat to a first temperature and/or cool a portion of the transdermal delivery system so as to provide pulsatile delivery of the first active agent through the transdermal membrane,
   wherein the temperature control element is further configured to cyclically heat to a second temperature, different from the first temperature, the portion of the transdermal delivery system so as to provide pulsatile delivery of a second active agent through the transdermal membrane.

2. The transdermal delivery system of claim 1, wherein the temperature control element comprises an electromagnetic energy source.

3. The transdermal delivery system of claim 1, wherein the temperature control element comprises a resistive element.

4. The transdermal delivery system of claim 1, wherein the temperature control element comprises an inductive coil or an electromagnet.

5. The transdermal delivery system of claim 1, wherein the temperature control element comprises a coolant or heat sink.

6. The transdermal delivery system of claim 1, wherein the portion of the transdermal membrane comprises a polymer configured to be heated or cooled to thereby change active agent flow.

7. The transdermal delivery system of claim 1, wherein the portion of the transdermal membrane comprises a glass transition polymer configured to be heated or cooled to thereby change active agent flow.

8. The transdermal delivery system of claim 1, wherein the portion of the transdermal membrane comprises a magnetic nanoparticle configured to be heated or cooled to thereby change active agent flow.

9. The transdermal delivery system of claim 1, wherein the first active agent comprises nicotine or a nicotine agonist.

10. The transdermal delivery system of claim 1, wherein the first active agent comprises a Parkinson's disease treatment.

11. The transdermal delivery system of claim 1, wherein the first active agent comprises at least one of benztropine, carbidopa, dopamine, a dopamine analog, a dopamine antagonist, a dopamine agonist, entacapone, levodopa (L-dopa), pramipexole, rasagiline, ropinirole, rotigotine, safinamide, selegiline, both carbidopa and levodopa, trihexyphenidyl and tolcapone.

12. The transdermal delivery system of claim 1, further comprising an adhesive in the transdermal membrane configured to adhere the transdermal membrane to the subject.

13. The transdermal delivery system of claim 1, further comprising an adhesive in the transdermal membrane, wherein the adhesive contains the first active agent.

14. The transdermal delivery system of claim 1, further comprising a temperature sensor configured to measure the temperature of at least one of the temperature control element, the portion of the transdermal delivery system, or the transdermal membrane.

15. The transdermal delivery system of claim 1, further comprising a power source configured to provide power to the temperature control element.

16. The transdermal delivery system of claim 1, further comprising a circuit board.

17. The transdermal delivery system of claim 1, further comprising a microcontroller configured to control delivery of a stimulus from the temperature control element.

18. The transdermal delivery system of claim 1, further comprising a communication element configured to receive or transmit data.

19. The transdermal delivery system of claim 18, wherein the communication element comprises Bluetooth or WiFi.

20. A method for transdermally delivering an active agent, comprising:
- cyclically heating to a first temperature and cooling a portion of a transdermal delivery system for a first amount of time; and
- after the first amount of time, cyclically heating to a second temperature and cooling the portion of the transdermal delivery system for a second amount of time,
- wherein the cyclic heating or cooling steps provide a pulsatile delivery of a first active agent from a reservoir based on the first temperature and a pulsatile deliver of a second active agent based on the second temperature, through a transdermal membrane of the transdermal delivery system to skin of a patient, wherein the transdermal membrane controls a flow of the first active agent and the second active agent in response to temperature.

21. The method of claim 20, wherein the cyclically heating or cooling steps comprise delivering heat to the portion of the transdermal delivery system.

22. The method of claim 20, wherein the cyclically heating or cooling steps comprise removing heat from the portion of the transdermal delivery system.

23. The method of claim 20, wherein at least one of the cyclically heating or cooling steps comprises delivering electromagnetic radiation to the portion of the transdermal delivery system.

24. The method of claim 20, further comprising repeating the cyclic heating or cooling steps at least once.

25. The method of claim 20, further comprising repeating the cyclic heating or cooling steps at least twice.

26. The method of claim 20, wherein the portion of the transdermal delivery system is increased in temperature by at least 4° C. during the cyclic heating and cooling steps.

27. The method of claim 20, further comprising actively heating skin of the subject adjacent the transdermal membrane by at least 3° C. during the cyclic heating or cooling steps.

28. The method of claim 20, wherein at least one of the actively heating or cooling steps is performed while the subject is sleeping.

29. A transdermal delivery system comprising:
- a transdermal membrane;
- a first active agent contained within a reservoir separate from and fluidically connected to the transdermal membrane, the transdermal membrane configured to control, in response to temperature, a flow of the active agent from the reservoir to skin of a subject; and
- a temperature control element configured to provide a first stimulus to a portion of the transdermal delivery system so as to provide pulsatile delivery of the first active agent through the transdermal membrane to the skin of the subject and provide a second stimulus to the portion of the transdermal delivery system so as to provide pulsatile delivery of a second active agent through the transdermal membrane, wherein the first stimulus is a first temperature and the second stimulus is a second temperature that is different than the first temperature.

30. The transdermal delivery system of claim 29, further comprising a reactive material configured to prevent the active agent from flowing across the transdermal membrane until the stimulus is applied.

31. The transdermal delivery system of claim 30, wherein the reactive material comprises an epoxy, a polyethylene, a polymethacrylate, a polypropylene, a polypropylene glycol, a polyvinylacetate, a polystyrene, a polytetrafluoroethylene, a poly(bisphenol A carbonate), a poly(ethylene terephthalate), a polylactic acid (PLA), a polyglycolic acid (PGA), or a polyurethane.

32. The transdermal delivery system of claim 30, wherein the reactive material comprises a polymer, a hydrogel, a solvent, gold covered nanoparticles, or magnetic nanoparticles.

* * * * *